(12) United States Patent
Bachmann et al.

(10) Patent No.: US 7,959,924 B2
(45) Date of Patent: *Jun. 14, 2011

(54) GASTRIC INHIBITORY POLYPEPTIDE (GIP) ANTIGEN ARRAYS AND USES THEREOF

(75) Inventors: Martin F. Bachmann, Seuzach (CH); Alma Fulurija, Zürich-Schlieren (CH); Philippe Saudan, Pfungen (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/461,206

(22) Filed: Aug. 4, 2009

(65) Prior Publication Data

US 2010/0143392 A1 Jun. 10, 2010

Related U.S. Application Data

(63) Continuation of application No. 11/257,498, filed on Oct. 25, 2005, now Pat. No. 7,572,451.

(60) Provisional application No. 60/621,465, filed on Oct. 25, 2004.

(51) Int. Cl.
*A61K 39/385* (2006.01)
*A61K 39/00* (2006.01)
*C12P 21/06* (2006.01)
*C07H 21/04* (2006.01)

(52) U.S. Cl. ............. 424/185.1; 424/193.1; 424/196.11; 435/69.1; 536/23.4; 536/23.51; 536/23.72

(58) Field of Classification Search ........................ None
See application file for complete search history.

(56) References Cited

U.S. PATENT DOCUMENTS

| 4,722,840 A | 2/1988 | Valenzuela et al. |
| 4,918,166 A | 4/1990 | Kingsman et al. |
| 5,143,726 A | 9/1992 | Thornton et al. |

(Continued)

FOREIGN PATENT DOCUMENTS

EP  0 479 210 A2  4/1992

(Continued)

OTHER PUBLICATIONS

Zorrilla, et al. Vaccination against weight gain. PNAS. 2006; 103(35): 13226-13231.*

(Continued)

*Primary Examiner* — Mary E Mosher
*Assistant Examiner* — Stuart W Snyder
(74) *Attorney, Agent, or Firm* — Sterne, Kessler, Goldstein & Fox P.L.L.C.

(57) ABSTRACT

The present invention is in the fields of medicine, public health, immunology, molecular biology and virology. The present invention provides, inter alia, a composition comprising a virus-like particle (VLP) and at least one antigen, wherein said antigen is a GIP protein or a GIP fragment linked to the VLP respectively.
The invention also provides a method for producing the aforesaid composition. The compositions of this invention are useful in the production of vaccines, in particular, for the prevention and/or treatment of obesity and hereby, in particular, by inducing efficient immune responses, in particular antibody responses. Furthermore, the compositions of the invention are particularly useful to efficiently induce self-specific immune responses within the indicated context. Accordingly, the invention further provides for methods of treating and/or preventing obesity and other conditions.

20 Claims, 2 Drawing Sheets

U.S. PATENT DOCUMENTS

| | | | |
|---|---|---|---|
| 5,580,859 | A | 12/1996 | Felgner et al. |
| 5,698,424 | A | 12/1997 | Mastico et al. |
| 5,928,647 | A | 7/1999 | Rock |
| 6,004,763 | A | 12/1999 | Gengoux et al. |
| 6,054,312 | A | 4/2000 | Larocca et al. |
| 6,159,728 | A | 12/2000 | Stockley et al. |
| 6,548,651 | B1 | 4/2003 | Nielsen et al. |
| 7,572,451 | B2 * | 8/2009 | Bachmann et al. ........ 424/185.1 |
| 2002/0064533 | A1 | 5/2002 | Murray |
| 2002/0081295 | A1 | 6/2002 | Schiller et al. |
| 2002/0193565 | A1 | 12/2002 | Stanley et al. |
| 2003/0054010 | A1 | 3/2003 | Sebbel et al. |
| 2003/0175290 | A1 | 9/2003 | Renner et al. |
| 2004/0076611 | A1 | 4/2004 | Bachmann et al. |
| 2004/0076645 | A1 | 4/2004 | Bachmann et al. |
| 2005/0191317 | A1 | 9/2005 | Bachmann et al. |
| 2005/0272652 | A1 | 12/2005 | Gault et al. |
| 2006/0121468 | A1 * | 6/2006 | Allnutt et al. ................... 435/6 |

FOREIGN PATENT DOCUMENTS

| | | |
|---|---|---|
| EP | 1 171 465 B1 | 1/2002 |
| WO | WO 99/08708 A2 | 2/1999 |
| WO | WO 99/57289 A2 | 11/1999 |
| WO | WO 00/20592 A1 | 4/2000 |
| WO | WO 00/23955 A1 | 4/2000 |
| WO | WO 00/32227 A2 | 6/2000 |
| WO | WO 00/58360 A2 | 10/2000 |
| WO | WO 01/85208 A2 | 11/2001 |
| WO | WO 02/10195 A2 | 2/2002 |
| WO | WO 02/094124 A2 | 11/2002 |
| WO | WO 03/030946 A1 | 4/2003 |
| WO | WO 03/060071 A2 | 7/2003 |
| WO | WO 03/103697 A2 | 12/2003 |
| WO | WO 2004/003143 A2 | 1/2004 |
| WO | WO 2004/004761 A2 | 1/2004 |
| WO | WO 2004/007538 A2 | 1/2004 |
| WO | WO 2004/009116 A2 | 1/2004 |
| WO | WO 2004/009124 A2 | 1/2004 |
| WO | WO 2005/082928 A2 | 9/2005 |
| WO | WO 2006/032674 A1 | 3/2006 |

OTHER PUBLICATIONS

Fulurija, et al. Vaccination against GIP for the Treatment of Obesity. PLoS One. 2008; 3(9):e3163,1-11.*

Baba, A.S.H., et al., "Effects of gastric inhibitory polypeptide, somatostatin and epidermal growth factor on lipogenesis in ovine adipose explants," *Comp. Biochem. Physiol. B. Biochem. Mol. Biol.* 127: 173-82, Elsevier Science Inc. (2000).

Bachmann, M.F., Zinkernagel, R.M., "The influence of virus structure on antibody responses and virus serotype formation," *Immunol. Today 17*: 553-8, Elsevier Science Publishers (1996).

Ballinger, A., "Gastric inhibitory polypeptide links overnutrition to obesity," *Gut* 52: 319-20, British Medical Ass. (Mar. 2003).

Brown, J.C., et al., "Preparation of highly active enterogastrone," *Can. J. Physiol. Pharmacol.* 47: 113-114, NRC Research Paper (1969).

Brown, W.L., et al., "RNA bacteriophage capsid-mediated drug delivery and epitope presentation," *Intervirology 45*: 371-80, Karger (2002).

Brubaker, P.L. and Drucker, D.J. "Structure-Function of the Glucagon Receptor Family of G Protein-Coupled Receptors: The Glucagon, GIP, GLP-1, and GLP-2 Receptors," *Recept. Channels 8*: 179-188, Taylor & Francis (2002).

Chackerian, B., et al., "Induction of autoantibodies to mouse CCR5 with recombinant papillomavirus particles," *Proc. Natl. Acad. Sci. USA 96*: 2373-2378, National Academy of Sciences (1999).

Creutzfeldt, W. and Ebert, R., "New developments in the incretin concept," *Diabetologia* 28: 565-573, Springer-Verlag (1985).

D'Alessio, D.A., et al., "Elimination of the Action of Glucagon-like Peptide 1 Causes an Impairment of Glucose Tolerance after Nutrient Ingestion by Healthy Baboons," *J. Clin. Invest.* 97: 133-138, American Society for Clinical Investigation (1996).

Drucker, D.J., "Enhancing Incretin Action for the Treatment of Type 2 Diabetes," *Diabetes Care 26*: 2929-2940, The American Diabetes Association (Oct. 2003).

Dupre, J., et al., "Stimulation of Insulin Secretion by Gastric Inhibitory Polypeptide in Man," *J. Clin. Endocrinol. Metab.* 37: 826-828, Endocrine Society (1973).

Ebert, R. and Creutzfeldt, W., "Influence of Gastric Inhibitory Polypeptide Antiserum on Glucose-Induced Insulin Secretion in Rats," *Endocrinology 111*: 1601-1606, The Endocrine Society (1982).

Elliott, R.M., et al., "Glucagon-like peptide-1 (7-36)amide and glucose-dependent insulinotropic polypeptide secretion in response to nutrient ingestion in man: acute post-prandial and 24-h secretion patterns," *J. Endocrinol.* 138: 159-166, Journal of Endocrinology Ltd (1993).

Fehr, T., et al., "T cell-independent type I antibody response against B cell epitopes expressed repetitively on recombinant virus particles," *Proc. Natl. Acad. Sci. USA*, 95: 9477-81, National Academy of Sciences (1998).

Fulurija, A., et al., "Vaccination against GIP for the Treatment of Obesity," *PLoS ONE 3*: e3163, Public Library of Science (Sep. 2008).

Gatto, D., et al., "Rapid Response of Marginal Zone B Cells to Viral Particles," *J. Immunol.* 173: 4308-4316, The American Association of Immunologists, Inc. (Oct. 2004).

Gault, V.A., et al., "Characterization of the Cellular and Metabolic Effects of a Novel Enzyme-Resistant Antagonist of Glucose-Dependent Insulinotropic Polypeptide," *Biochem. Biophys. Res. Commun.* 290: 1420-1426, Elsevier Science (2002).

Gault, V.A., et al., "Chemical Ablation of Gastric Inhibitory Polypeptide Receptor Action by Daily (Pro$^3$) GIP Administration Improves Glucose Tolerance and Ameliorates Insulin Resistance and Abnormalities of Islet Structure in Obesity-Related Diabetes," *Diabetes 54*: 2436-2446, American Diabetes Association (Aug. 2005).

Gault, V.A., et al., "DPP IV resistance and insulin releasing activity of a novel di-substituted analogue of glucose-dependent insulinotropic polypeptide, (Ser$^2$-Asp$^{13}$)GIP," *Cell Biol. Int.* 27:41-46, Elsevier Science Ltd. (Jan. 2003).

Gault, V.A., et al., "Glucose-dependent insulinotropic polypeptide (GIP): anti-diabetic and anti-obesity potential?," *Neuropeptides 37*: 253-63, Elsevier Ltd. (Oct. 2003).

Gault, V.A., et al., "Glucose-dependent insulinotropic polypeptide analogues and their therapeutic potential for the treatment of obesity-diabetes," *Biochem. Biophys. Res. Commun. 308*: 207-213, Elsevier Inc. (Aug. 2003).

Gelling, R.W., et al., "GIP$_{6-30amide}$ contains the high affinity binding region of GIP and is a potent inhibitor of GIP$_{1-42}$ action in vitro," *Regul. Pept. 69*: 151-154, Elsevier Science (1997).

Hinke, S.A., et al., "Dipeptidyl Peptidase IV-Resistant [D-Ala$^2$]Glucose-Dependent Insulinotropic Polypeptide (GIP) Improves Glucose Tolerance in Normal and Obese Diabetic Rats," *Diabetes 51*: 652-661, American Diabetes Association (2002).

Hinke, S.A., et al., "Identification of a bioactive domain in the amino-terminus of glucose-dependent insulinotropic polypeptide (GIP)," *Biochim. Biophys. Acta. 1547*: 143-155, Elsevier Science B.V. (2001).

Hinke, S.A., et al., "In depth analysis of the N-terminal bioactive domain of gastric inhibitory polypeptide," *Life Sci.* 75: 1857-1870, Elsevier Inc. (Aug. 2004).

Hofmann, R.M. and T.W. Muir, "Recent advances in the application of expressed protein ligation to protein engineering," *Curr. Opin. Biotech.* 13: 297-303, Elsevier Science Ltd. (2002).

Holst, J.J., et al., "Depression of Insulin Release with Anti-GIP Serum After Oral Glucose in Rats," Abstract S52 (2003).

Hu, Y.-C., et al., "Chimeric Infectious Bursal Disease Virus-like Particles Expressed In Insect Cells and Purified by Immobilized Metal Affinity Chromatography," *Biotech. Bioeng. 63*: 722-730, John Wiley & Sons, Inc. (1999).

Jegerlehner, A., et al., "A molecular assembly system that renders antigens of choice highly repetitive for induction of protective B cell responses," *Vaccine 20*: 3104-12, Elsevier Science (2002).

Jörnvall, H., et al., "Amino Acid Sequence and Heterogeneity of Gastric Inhibitory Polypeptide (GIP)," *FEBS Lett. 123*: 205-210, Elsevier/North-Holland Biomedical Press (1981).

Kieffer, T.J., "GIP or not GIP? That is the question," *Trends Pharmacol. Sci. 24*: 110-112, Elsevier Science Ltd. (Mar. 2003).

Klovins, J., et al., "Nucleotide sequence of a ssRNA phage from *Acinetobacter*: kinship to coliphages," *J Gen Virol 83*: 1523-33, Society For General Microbiology (2002).

Kozlovska, T.M., et al., "RNA Phage Qβ Coat Protein as a Carrier for Foreign Epitopes," *Intervirology 39*: 9-15, S. Karger AG, Basel (1996).

Kozlovska, T.M., et al. "Recombinant RNA phage Qβ capsid particles synthesized and self-assembled in *Escherichia coli*," *Gene 137*: 133-7, Elsevier Science Publishers B.V. (1993).

Lardinois, C.K., et al., "The Postprandial Response of Gastric Inhibitory Polypeptide to Various Dietary Fats in Man," *J. Am. Coll. Nutr. 7*: 241-7, John Wiley & Sons, Inc. (1988).

Lauritsen, K.B., et al., "Depression of Insulin Release by Anti-GIP Serum after Oral Glucose in Rats," *Scand. J. Gastroenterol. 16*: 417-420, Universitetsforlaget (1981).

Lechner, F., et al., "Virus-like particles as a modular system for novel vaccines," *Intervirology 45*: 212-7, Karger (2002).

Lewis, J.T., et al., "Glucose-Dependent Insulinotropic Polypeptide Confers Early Phase Insulin Release to Oral Glucose in Rats: Demonstration by a Receptor Antagonist," *Endocrinology 141*: 3710-3716, The Endocrine Society (2000).

Loktev, V.B., et al., "Design of immunogens as components of a new generation of molecular vaccines," *J. Biotechnol. 44*: 129-37, Elsevier Science B.V. (1996).

Lu, M., et al., "The Role of the Free Cytosolic Calcium Level in β-Cell Signal Transduction by Gastric Inhibitory Polypeptide and Glucagon-Like Peptide I(7-37)," *Endocrinology 132*: 94-100, The Endocrine Society (1993).

Maletti, M., et al., "Structural Requirements for Gastric Inhibitory Polypeptide (GIP) Receptor Binding and Stimulation of Insulin Release," *Peptides 7 Suppl.1*: 75-78, Ankho International Inc. (1986).

Manhart, S., et al., "Structure-Function Analysis of a Series of Novel GIP Analogues Containing Different Helical Length Linkers," *Biochemistry 42*: 3081-3088, American Chemical Society (Feb. 2003).

Miyawaki, K., et al., "Glucose intolerance caused by a defect in the entero-insular axis: a study in gastric inhibitory polypeptide receptor knockout mice," *Proc. Natl. Acad. Sci. USA 96*: 14843-14847, National Academy of Sciences (1999).

Miyawaki, K., et al., "Inhibition of gastric inhibitory polypeptide signaling prevents obesity," *Nat. Med. 8*: 738-42, Nature Publishing Group (2002).

Moody, A.J., et al., "The isolation and sequencing of human gastric inhibitory peptide (GIP)," *FEBS Lett. 172*: 142-148, Elsevier Science Publishers B.V. (1984).

Neel, J., "The 'Thrifty Genotype' in 1998," *Nutr. Rev. 57*: S2-S9, International Life Sciences Institute (1999).

Nieland, J.D., et al. "Chimeric papillomavirus virus-like particles induce a murine self-antigen-specific protective and therapeutic antitumor immune response," *J. Cell. Biochem.* 73: 145-52, Wiley-Liss, Inc. (1999).

Stoll, E., et al., "Revised amino acid sequence of Qβ coat protein between positions 1 and 60," *J. Biol. Chem.*, 252: 990-3, American Society for Biochemistry and Molecular Biology (1977).

Takeda, J., et al., "Sequence of an intestinal cDNA encoding human gastric inhibitory polypeptide precursor," *Proc. Natl. Acad. Sci. USA 84*: 7005-7008, National Academy of Sciences (1987).

Tseng, C.C. et al., "Glucose-dependent insulinotropic peptide: structure of the precursor and tissue-specific expression in rat," *Proc. Natl. Acad. Sci. USA 90*: 1992-1996, National Academy of Sciences (1993).

Tseng, C.C. et al., "Postprandial Stimulation of Insulin Release by Glucose-dependent Insulinotropic Polypeptide (GIP). Effect of a Specific Glucose-Dependent Insulinotropic Polypeptide Receptor Antagonist in the Rat," *J. Clin. Invest. 98*: 2440-2445, The American Society for Clinical Investigation, Inc. (1996).

Usdin, T.B., et al., "Gastric Inhibitory Polypeptide Receptor, a Member of the Secretin-Vasoactive Intestinal Peptide Receptor Family, Is Widely Distributed in Peripheral Organs and the Brain," *Endocrinology 133*: 2861-2870, The Endocrine Society (1993).

Vasiljeva, I., et al., "Mosaic Qβ coats as a new presentation model," *FEBS Lett.* 431: 7-11, Federation of European Biochemical Societies (1998).

Voronkova, T., et al., "Chimeric bacteriophage fr virus-like particles harboring the immunodominant C-terminal region of hamster polyomavirus VP1 induce a strong VP1-specific antibody response in rabbits and mice," *Viral Immunol.*, 15: 627-43, Mary Ann Liebert, Inc. (2002).

Yip, R.G.C. and Wolfe, M.M., "GIP Biology and Fat Metabolism," *Life Sci. 66*: 91-103, Elsevier Science Inc. (2000).

Yip, R.G.-C., et al., "Functional GIP Receptors are Present on Adipocytes," *Endocrinology 139*: 4004-4007, The Endocrine Society (1998).

Zorrilla, E.P., et al., "Vaccination against weight gain," *Proc. Natl. Acad. Sci. USA*, 103: 13226-13231, National Academy of Sciences (Aug. 2006).

Notice of Allowance (Notice of Allowability) mailed Apr. 7, 2009, in U.S. Appl. No. 11/257,498, Bachmann, M., et al., filed Oct. 25, 2005.

Office Action mailed Apr. 29, 2008, in U.S. Appl. No. 11/257,498, Bachmann, M., et al., filed Oct. 25, 2005.

Office Action mailed Apr. 30, 2007, in U.S. Appl. No. 11/257,498, Bachmann, M., et al., filed Oct. 25, 2005.

\* cited by examiner

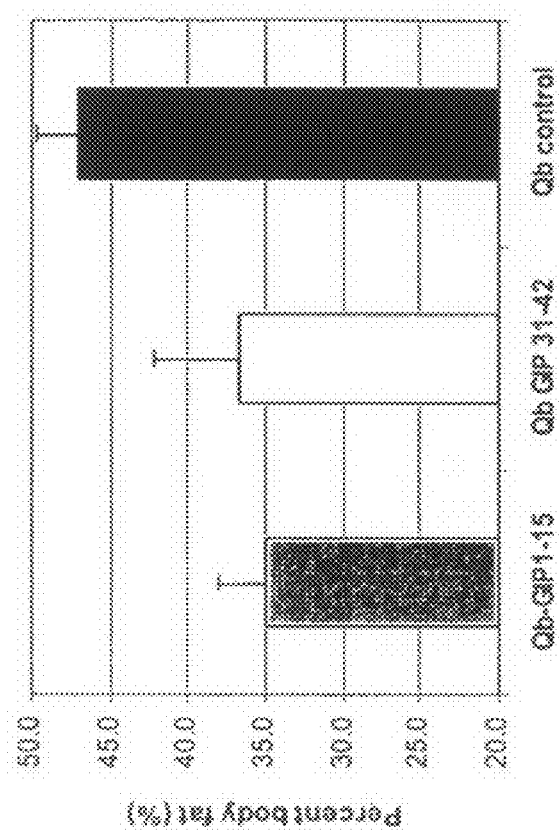
FIG 2B
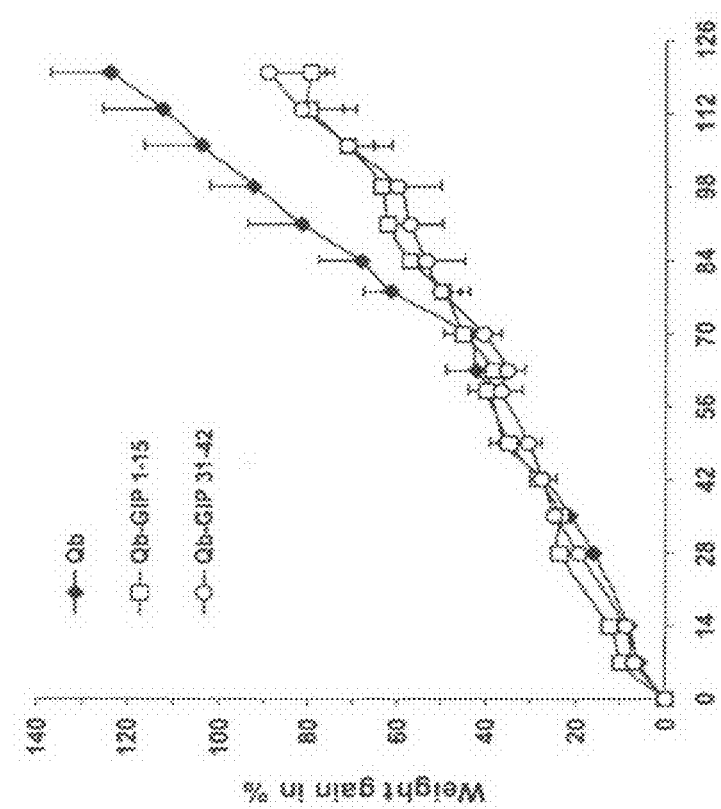
FIG 2A
FIG 2

GASTRIC INHIBITORY POLYPEPTIDE (GIP) ANTIGEN ARRAYS AND USES THEREOF

CROSS REFERENCE TO RELATED APPLICATIONS

This application is a continuation of U.S. application Ser. No. 11/257,498, filed Oct. 25, 2005, which claims the benefit of the filing date of U.S. Provisional Application No. 60/621,465, filed Oct. 25, 2004, the disclosures of each of which are entirely incorporated herein by reference.

BACKGROUND OF THE INVENTION

1. Field of the Invention

The present invention is in the fields of medicine, public health, immunology, molecular biology and virology. The present invention provides, inter alia, a composition comprising a virus-like particle (VLP) and at least one antigen, wherein said antigen is a GIP protein or a GIP fragment linked to the VLP respectively.

The invention also provides a method for producing the aforesaid composition. The compositions of this invention are useful in the production of vaccines, in particular, for the prevention and/or treatment of obesity and hereby, in particular, by inducing efficient immune responses, in particular antibody responses. Furthermore, the compositions of the invention are particularly useful to efficiently induce self-specific immune responses within the indicated context.

2. Related Art

Glucose-dependent insulinotropic polypeptide (GIP, also known as gastric inhibitory polypeptide) is a gastrointestinal hormone that is released during a meal from endocrine K-cells that line the gut wall. The amount of GIP that is released into the blood is largely dependent on meal content and is induced primarily by the absorption of ingested fat, glucose or amino acids (Elliott, R. M: et al, (1993), J. Endocrinol. 138, 159-166, Lardinois, C. K. et al, (1988), J Am Coll Nutr. 7(3), 241-7). GIP acts rapidly on pancreatic β-cells to stimulate the release of insulin, thereby ensuring prompt insulin-mediated uptake of glucose into tissues (Dupré J. et al, (1973) J. Clin. Endocrinol. Metab. 37, 826-828). GIP achieves this effect by binding to a seven-transmembrane G-protein-coupled receptor expressed on β-cells. Once bound by GIP, these receptors activate adenylyl cyclase and other signal transduction pathways, ultimately leading to the elevation of intracellular Ca2+ concentrations and insulin exocytosis (Lu, M. et al, (1993), Endocrinology 133, 2861-2870). In addition to fat and glucose intake, ingestion of carbohydrates also stimulates GIP release (Elliott, R. M: et al, (1993), J. Endocrinol. 138, 159-166).

GIP is considered to be one of the principle incretin factors of the entero-insular axis. It has been described that anti-GIP antibodies block the action of GIP on glucose induced insulin secretion (Ebert et al, Endocrinology (1982) 111: 1601). Moreover, GIP has also been postulated to act directly on adipocytes, which express the GIP receptor (Yip et al, Endocrinology (1998) 139: 4004).

Due to its insulinotropic activity, there has been considerable interest in utilising the hormone as a potential therapy for type 2 diabetes (EP171465, WO03/030946). Furthermore, it has recently been shown that GIP receptor knock-out mice (GIPR−/−) have higher blood glucose levels with impaired initial insulin response after oral glucose load. Although blood glucose levels after ingestion are not increased by high-fat diet in GIPR+/+ mice because of compensatory higher insulin secretion, they are significantly increased in GIPR−/− mice because of the lack of such enhancement. Accordingly, a defect in this entero-insular axis may contribute to the pathogenesis of diabetes (Miyawaki K. et al, (1999) PNAS 96:26, 14843-14847).

The same research group later showed that wild-type mice fed a high-fat diet exhibited both hypersecretion of GIP and extreme visceral and subcutaneous fat deposition with insulin resistance. In contrast, mice lacking the GIP receptor (GIPR−/−) fed a high-fat diet were protected from both the development of obesity and insulin resistance (Miyawaki K. et al, (2002) Nature Medicine 8: 7, 738-742). However, several studies have observed impaired insulin secretion and hyperglycemia in rodents following nutrient ingestion when GIP action is acutely disrupted with GIP receptor antagonists (Lewis, J. T. et al (2000), Endocrinology 141, 3710-3716; Tseng, C. C. et al (1996) J. Clin. Invest. 98, 2440-2445). This suggests that chronic treatment with a GIP receptor antagonist might result in glucose intolerance, or even in diabetes (Kieffer, T. J. (2003), Trends in Pharmacological Sciences Vol. 24 No. 3, 110-112).

SUMMARY OF THE INVENTION

We have, now, surprisingly found that the inventive compositions and vaccines, respectively, comprising a GIP protein or a GIP fragment are capable of inducing strong immune responses, in particular strong antibody responses, leading to high antibody titer against the self-antigen GIP. Moreover, we have surprisingly found that inventive compositions and vaccines, respectively, comprising a GIP protein or a GIP fragment are capable of inducing strong immune responses, in particular strong antibody responses, in obese mice fed a high-fat diet in both prophylactic setting and in therapeutic setting. The weight gain of these obese mice that received the inventive compositions and vaccines, respectively, has been significantly reduced, compared to mice that did not receive the inventive compositions and vaccines, respectively. This indicates that the immune responses, in particular the antibodies generated by the inventive compositions and vaccines, respectively, are thus capable of specifically recognizing GIP in vivo and interfere with its function. Moreover, since antibodies are large molecules which only inefficiently penetrate solid tissue, in particular fat tissue, it was highly surprising that the compositions and vaccines of the invention are effective at inhibiting the build up of fat stores.

We have further surprisingly found that the inventive compositions and vaccines, while being effective in interfering with the GIP function in vivo, in particular in protecting the recipient animals from gaining weight, does not interfere with blood glucose, plasma triglyceride and fructosamine levels, indicating that the compositions of the invention does not lead to diabetes. Thus the inventive compositions and vaccines are proven to be safe for the use in preventing or treating obesity.

Thus, in a first aspect, the present invention provides a composition which comprises (a) a virus-like particle (VLP), with at least one first attachment site; and (b) at least one GIP protein or at least one GIP fragment with at least one second attachment site, wherein (a) and (b) are linked through the first and the second attachment sites, preferably to form an ordered and repetitive antigen array. In preferred embodiments of the invention, the virus-like particles suitable for use in the present invention comprises recombinant protein, preferably recombinant coat protein, mutants or fragments thereof, of a virus, preferably of a RNA bacteriophage.

In one preferred embodiment, the inventive composition comprises a GIP fragment. While ensuring a strong and protective immune response, in particular an antibody response, the use of GIP fragments for the present invention may reduce a possible induction of self-specific cytotoxic T cell responses and may reduce the production cost of the inventive compositions and vaccines, respectively.

In another aspect, the present invention provides a vaccine composition. Furthermore, the present invention provides a method to administering the vaccine composition to a human or an animal, preferably a mammal. The vaccine of the present invention is capable of inducing a strong immune response, in particular an antibody response, without the presence of any adjuvant. Thus, in one preferred embodiment, the vaccine is devoid of any adjuvant. The avoidance of using adjuvant may reduce a possible occurrence of unwanted inflammatory T cell responses.

In a further aspect, the present invention provides for a pharmaceutical composition comprising the inventive composition and an acceptable pharmaceutical carrier.

In a still further aspect, the present invention provides for a method of preventing, alleviating or effectively treating, in particular, obesity.

In one further aspect, the invention provides a method for treating obesity in an animal, preferably a domestic cat or a dog, or a human comprising administering the vaccine of the invention and the vaccine of VLP-ghrelin to the same animal or human. In one preferred embodiment of the invention, the vaccine of the invention and the vaccine of VLP-ghrelin are administered contemporaneously to the same animal or human. In one further aspect, the invention provides a method for preventing and treating obesity, preferably preventing obesity in human comprising administering the vaccine of the invention and the vaccine of VLP-nicotine to the same human. This is to preferably compensate the increase of body weight after smoking cessation. Further preferably, this is to compensate the increase of food intake during and after the smoking cessation. The administering two vaccines to the same animal or human may additively, or preferably synergistically, increase the efficacy of each vaccine when administered individually.

BRIEF DESCRIPTION OF THE DRAWINGS

FIG. 2 shows the efficacy of GIP 1-15-GC-Qβ or Qβ-CG-GIP 31-42 vaccine in mice. C57BL/6 mice were vaccinated either murine GIP 1-15-GC, murine CG-GIP 31-42 coupled to Qβ VLP, or Qβ VLP only, as described in detail in EXAMPLE 6. FIG. 2A shows the weight gain of these mice over a period of time as indicated in the x-axis and FIG. 2B shows the fat composition of these mice 142 days after the first immunization.

DETAILED DESCRIPTION OF THE INVENTION

Figure 1:
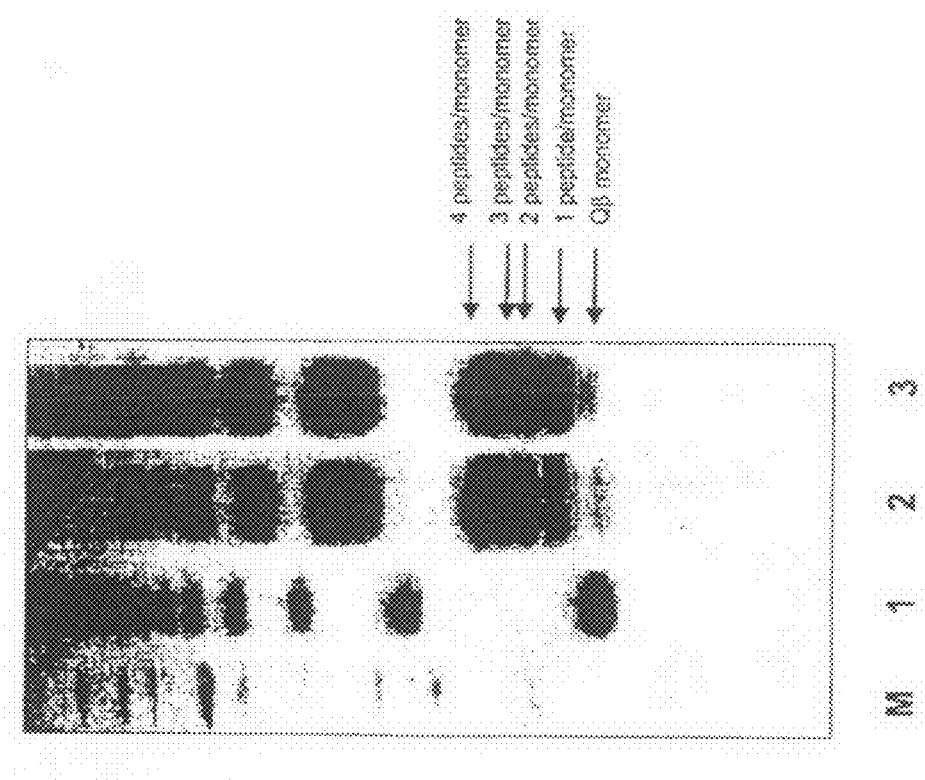
FIG. 1. shows the coupling of GIP fragments to the Qβ VLP on a reducing SDS-PAGE gel. Lane M is the molecular marker; Lane 1 is the derivatized Qβ monomer; Lane 2 is the GIP fragment 1-15 GC coupled to the Qβ monomer; Lane 3 is the GIP fragment 31-42 GC coupled to the Qβ monomer. Coupling bands corresponding to one, two, three or four peptides coupled per subunit are indicated by arrows.

Antigen: As used herein, the term "antigen" refers to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

Antigenic site: The term "antigenic site" and the term "antigenic epitope", which are used herein interchangeably, refer to continuous or discontinuous portions of a polypeptide, which can be bound immunospecifically by an antibody or by a T-cell receptor within the context of an MHC molecule. Immunospecific binding excludes non-specific binding but does not necessarily exclude cross-reactivity. Antigenic site typically comprise 5-10 amino acids in a spatial conformation which is unique to the antigenic site.

Associated: The term "associated" (or its noun association) as used herein refers to all possible ways, preferably chemical interactions, by which two molecules are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, amide, peptide, carbon-phosphorus bonds, carbon-sulfur bonds such as thioether, or imide bonds.

Attachment Site, First: As used herein, the phrase "first attachment site" refers to an element which is naturally occurring with the VLP or which is artificially added to the VLP, and to which the second attachment site may be linked. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the first attachment site is the amino group of an amino acid such as lysine. The first attachment site is located, typically on the surface, and preferably on the outer surface of the VLP. Multiple first attachment sites are present on the surface, preferably on the outer surface of virus-like particle, typically in a repetitive configuration. In a preferred embodiment the first attachment site is associated with the VLP, through at least one covalent bond, preferably through at least one peptide bond.

Attachment Site, Second: As used herein, the phrase "second attachment site" refers to an element which is naturally occurring with or which is artificially added to the GIP of the invention and to which the first attachment site may be linked. The second attachment site of GIP of the invention may be a protein, a polypeptide, a peptide, an amino acid, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the second attachment site is the sulfhydryl group, preferably of an amino acid cysteine. The terms "GIP protein with at least one second attachment site", "GIP fragment with at least one second attachment site" or "GIP of the invention with at least one second attachment site" refer, therefore, to a construct comprising the GIP of the invention and at least one second attachment site. However, in particular for a second attachment site, which is not naturally occurring with the GIP protein or the GIP fragment, such a construct typically and preferably further comprises a "linker". In another preferred embodiment the second attachment site is associated with the GIP of the invention through at least one covalent bond, preferably through at least one peptide bond. In yet another preferred embodiment, the second attachment site is artificially added to the GIP of the invention through an amino acid linker, preferably comprising a cysteine, by protein fusion.

Bound: As used herein, the term "bound" refers to binding that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term also includes the enclosement, or partial enclosement, of a substance. The term "bound" is broader than and includes terms such as "coupled," "fused," "enclosed", "packaged" and "attached." For example, the polyanionic macromolecule such as the polyglutamic acid can be, and typically and preferably is, enclosed or packaged by the VLP, typically and preferably without the existence of an actual covalent binding.

Coat protein: The term "coat protein" and the interchangeably used term "capsid protein" within this application, refers to a viral protein, which is capable of being incorporated into a virus capsid or a VLP. Typically and preferably the term "coat protein" refers to the coat protein encoded by the genome of a virus, preferably an RNA bacteriophage or by the genome of a variant of a virus, preferably of an RNA bacteriophage. More preferably and by way of example, the term "coat protein of AP205" refers to SEQ ID NO:14 or the amino acid sequence, wherein the first methionine is cleaved from SEQ ID NO:14. More preferably and by way of example, the term "coat protein of Qβ" refers to SEQ ID NO:1 ("Qβ CP") and SEQ ID NO:2 (A1), with or without the methione at the N-terminus. The capsid of bacteriophage Qβ is composed mainly of the Qβ CP, with a minor content of the A1 protein.

GIP of the invention: The term "GIP of the invention" as used herein, refers to at least one GIP protein or at least one GIP fragment as defined herein.

GIP protein: The term "GIP protein" as used herein should encompass any polypeptide comprising, or alternatively or preferably consisting of, the human GT of SEQ ID NO:22, the mouse GIP of SEQ ID NO:23, the rat GIP of SEQ ID NO:24, the bovine GIP of SEQ ID NO:25, the pig GIP of SEQ ID NO:26, the cat or dog GIP of SEQ ID NO:63 or the corresponding GIP sequence of any ortholog from any other animal. The term "ortholog" denotes a polypeptide obtained from one species that is the functional counterpart of a polypeptide from a different species. Sequence differences among orthologs are the result of speciation. Moreover, the term "GIP protein" as used herein should also encompass any polypeptide comprising, or alternatively or preferably consisting of, any natural or genetic engineered variant having more than 70%, preferably more than 80%, preferably more than 85%, even more preferably more than 90%, again more preferably more than 95%, and most preferably more than 97% amino acid sequence identity with the human GIP of SEQ ID NO:22, the mouse GIP of SEQ ID NO:23, the rat GIP of SEQ ID NO:24, the bovine GIP of SEQ ID NO:25, the pig GIP of SEQ ID NO:26, the cat or dog GIP of SEQ ID NO:63 or the corresponding orthologs from any other animal. The term "GIP protein" as used herein should furthermore encompass post-translational modifications including but not limited to glycosylations, acetylations, phosphorylations of the GIP protein as defined above. Preferably the GIP protein, as defined herein, consists of at most 200 amino acids in length, and even more preferably of at most 100 amino acids, still more preferably at most 50 amino acids in length. Typically and preferably, GIP protein linked to VLPs should be capable of inducing the production of antibodies in vivo specifically capable of binding to GIP, as verified by, for example ELISA.

GIP fragment: The term "GIP fragment" as used herein should encompass any polypeptide comprising, or alternatively or preferably consisting of, at least 4, 5, 6, 7, 8, 9, 10, 11 or 12 contiguous amino acids of a GIP protein as defined herein as well as any polypeptide having more than 65%, preferably more than 80%, preferably more than 85%, more preferably more than 90% and even more preferably more than 95% amino acid sequence identity thereto. Preferably, the term "GIP fragment" as used herein should encompass any polypeptide comprising, or alternatively or preferably consisting of, at least 6 contiguous amino acids of a GIP protein as defined herein as well as any polypeptide having more than 80%, preferably more than 85%, preferably more than 90% and even more preferably more than 95% amino acid sequence identity thereto. Preferred embodiments of GIP fragment are truncation or internal deletion forms of GIP protein. Typically and preferably, GIP fragment linked to VLPs should be capable of inducing the production of antibodies, in vivo, specifically capable of binding to GIP.

The amino acid sequence identity of polypeptides can be determined conventionally using known computer programs such as the Bestfit program. When using Bestfit or any other sequence alignment program, preferably using Bestfit, to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, polypeptides or a fragment thereof disclosed in this invention.

Linked: The term "linked" (or its noun: linkage) as used herein, refers to all possible ways, preferably chemical interactions, by which the at least one first attachment site and the at least one second attachment site are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, amide, peptide, carbon-phosphorus bonds, carbon-sulfur bonds such as thioether, or imide bonds. In certain preferred embodiments the first attachment site and the second attachment site are linked through at least one covalent bond, preferably through at least one non-peptide bond, and even more preferably through exclusively non-peptide bond(s). The term "linked" as used herein, however, shall not only encompass a direct linkage of the at least one first attachment site and the at least one second attachment site but also, alternatively and preferably, an indirect linkage of the at least one first attachment site and the at least one second attachment site through intermediate molecule(s), and hereby typically and preferably by using at least one, preferably one, heterobifunctional cross-linker.

Linker: A "linker", as used herein, either associates the second attachment site with GIP of the invention or already comprises, essentially consists of, or consists of the second attachment site. Preferably, a "linker", as used herein, already comprises the second attachment site, typically and preferably—but not necessarily—as one amino acid residue, preferably as a cysteine residue. A "linker" as used herein is also termed "amino acid linker", in particular when a linker according to the invention contains at least one amino acid residue. Thus, the terms "linker" and "amino acid linker" are interchangeably used herein. However, this does not imply that such a linker consists exclusively of amino acid residues, even if a linker consisting of amino acid residues is a preferred embodiment of the present invention. The amino acid residues of the linker are, preferably, composed of naturally occurring amino acids or unnatural amino acids known in the art, all-L or all-D or mixtures thereof. Further preferred embodiments of a linker in accordance with this invention are molecules comprising a sulfhydryl group or a cysteine residue and such molecules are, therefore, also encompassed within this invention. Further linkers useful for the present invention are molecules comprising a C1-C6 alkyl-, a cycloalkyl such as a cyclopentyl or cyclohexyl, a cycloalkenyl, aryl or heteroaryl moiety. Moreover, linkers comprising preferably a C1-C6 alkyl-, cycloalkyl-(C5, C6), aryl- or heteroaryl-moiety and additional amino acid(s) can also be used as linkers for the present invention and shall be encompassed within the scope of the invention. Association of the linker with the GIP of the invention is preferably by way of at least one covalent bond, more preferably by way of at least one peptide bond.

Ordered and repetitive antigen array: As used herein, the term "ordered and repetitive antigen array" generally refers to a repeating pattern of antigen, characterized by a typically and preferably high order of uniformity in spacial arrangement of the antigens with respect to virus-like particle, respectively. In one embodiment of the invention, the repeating pattern may be a geometric pattern. Certain embodiments of the invention, such as VLP of RNA phages, are typical and preferred examples of suitable ordered and repetitive antigen arrays which, moreover, possess strictly repetitive paracrystalline orders of antigens, preferably with spacings of 1 to 30 nanometers, preferably 2 to 15 nanometers, even more preferably 2 to 10 nanometers, even again more preferably 2 to 8 nanometers, and further more preferably 1.6 to 7 nanometers.

Packaged: The term "packaged" as used herein refers to the state of a polyanionic macromolecule in relation to the VLP. The term "packaged" as used herein includes binding that may be covalent, e.g., by chemically coupling, or non-covalent, e.g., ionic interactions, hydrophobic interactions, hydrogen bonds, etc. The term also includes the enclosement, or partial enclosement, of a polyanionic macromolecule. Thus, the polyanionic macromolecule can be enclosed by the VLP without the existence of an actual binding, in particular of a covalent binding. In preferred embodiments, the at least one polyanionic macromolecule is packaged inside the VLP, most preferably in a non-covalent manner.

Polypeptide: The term "polypeptide" as used herein refers to a molecule composed of monomers (amino acids) linearly linked by amide bonds (also known as peptide bonds). It indicates a molecular chain of amino acids and does not refer to a specific length of the product. Thus, peptides, dipeptides, tripeptides, oligopeptides and proteins are included within the definition of polypeptide. Post-translational modifications of the polypeptide, for example, glycosylations, acetylations, phosphorylations, and the like are also encompassed.

Virus particle: The term "virus particle" as used herein refers to the morphological form of a virus. In some virus types it comprises a genome surrounded by a protein capsid; others have additional structures (e.g., envelopes, tails, etc.).

Virus-like particle (VLP), as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. Preferably a virus-like particle in accordance with the invention is non-replicative and/or non-infectious since it lacks all or part of the viral genome or genome function. In one embodiment, a virus-like particle is a virus particle, in which the viral genome has been physically or chemically inactivated. Typically and more preferably a virus-like particle lacks all or part of the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, preferably RNA-phage. The terms "viral capsid" or "capsid", refer to a macromolecular assembly composed of viral protein subunits. Typically, there are 60, 120, 180, 240, 300, 360 and more than 360 viral protein subunits. Typically and preferably, the interactions of these subunits lead to the formation of viral capsid or viral-capsid like structure with an inherent repetitive organization, wherein said structure is, typically, spherical or tubular.

Virus-like particle of a RNA phage: As used herein, the term "virus-like particle of a RNA phage" refers to a virus-like particle comprising, or preferably consisting essentially of or consisting of coat proteins, mutants or fragments thereof, of a RNA phage. In addition, virus-like particle of a RNA phage resembling the structure of a RNA phage, being non replicative and/or non-infectious, and lacking at least the gene or genes encoding for the replication machinery of the RNA phage, and typically also lacking the gene or genes encoding the protein or proteins responsible for viral attachment to or entry into the host. This definition should, however, also encompass virus-like particles of RNA phages, in which the aforementioned gene or genes are still present but inactive, and, therefore, also leading to non-replicative and/or non-infectious virus-like particles of a RNA phage. Within this present disclosure the term "subunit" and "monomer" are interexchangeably and equivalently used within this context. In this application, the term "RNA-phage" and the term "RNA-bacteriophage" are interchangeably used.

One, a, or an: when the terms "one", "a", or "an" are used in this disclosure, they mean "at least one" or "one or more" unless otherwise indicated.

Within this application, antibodies are defined to be specifically binding if they bind to the antigen with a binding affinity (Ka) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The affinity of an antibody can be readily determined by one of ordinary skill in the art (for example, by Scatchard analysis.)

This invention provides compositions and methods for enhancing immune responses against GIP in an animal or in human. Compositions of the invention comprises: (a) a virus-like particle (VLP) with at least one first attachment site; and (b) at least one antigen with at least one second attachment site, wherein the at least one antigen is a GIP protein or a GIP fragment and wherein (a) and (b) are linked through the at least one first and the at least one second attachment site. Preferably, the GIP protein or the GIP fragment is linked to the VLP, so as to form an ordered and repetitive antigen-VLP array. In preferred embodiments of the invention, at least 30, more preferably at least 60, again more preferably at least 120 and further more preferably at least 180 GIP of the invention are linked to the VLP.

Any virus known in the art having an ordered and repetitive structure may be selected as a VLP of the invention. Illustrative DNA or RNA viruses, the coat or capsid protein of which can be used for the preparation of VLPs have been disclosed in WO 2004/009124 on page 25, line 10-21, on page 26, line 11-28, and on page 28, line 4 to page 31, line 4. These disclosures are incorporated herein by way of reference.

Virus or virus-like particle can be produced and purified from virus-infected cell culture. The resulting virus or virus-like particle for vaccine purpose needs to be devoid of virulence. Avirulent virus or virus-like particle may be generated by chemical and/or physical inactivation, such as UV irradiation, formaldehyde treatment. Alternatively, the genome of the virus may be genetically manipulated by mutations or deletions to render the virus replication incompetent.

In one preferred embodiment, the VLP is a recombinant VLP. Recombinant VLP as disclosed herein, refers to a VLP which is prepared by a process comprising at least one step of DNA recombination technology. Almost all commonly known viruses have been sequenced and are readily available to the public. The gene encoding the coat protein can be easily identified by a skilled artisan. Typically, the coat protein gene can be cloned by standard methods into an expression vector and expressed in a vector-suitable host. The VLP, resulted from the self assembly of the expressed coat protein can be recovered and further purified by methods commonly known in the art. Examples have been disclosed in WO02/056905 and are herein incorporated by way of reference: Suitable host cells for virus-like particle production on page 29, line 37, to page 30, line 12; methods for introducing polynucleotide vectors into host cells on page 30, lines 13-27 and mammalian cells as recombinant host cells for the production of virus-like particles on page 30, lines 28-35.

In one preferred embodiment, the virus-like particle comprises, or alternatively consists of, recombinant proteins, mutants or fragments thereof, of a virus selected form the group consisting of: a) RNA phages; b) bacteriophages; c) Hepatitis B virus, preferably its capsid protein (Ulrich, et al., Virus Res. 50:141-182 (1998)) or its surface protein (WO 92/11291); d) measles virus (Warnes, et al., Gene 160:173-178 (1995)); e) Sindbis virus; f) rotavirus (U.S. Pat. No. 5,071,651 and U.S. Pat. No. 5,374,426); g) foot-and-mouth-disease virus (Twomey, et al., Vaccine 13:1603 1610, (1995)); h) Norwalk virus (Jiang, X., et al., Science 250:1580 1583 (1990); Matsui, S. M., et al., J. Clin. Invest. 87:1456 1461 (1991)); i) Alphavirus; j) retrovirus, preferably its GAG protein (WO 96/30523); k) retrotransposon Ty, preferably the protein p1; l) human Papilloma virus (WO 98/15631); m) Polyoma virus; n) Tobacco mosaic virus; and o) Flock House Virus.

In one preferred embodiment, the VLP comprises, or consists of, more than one amino acid sequence, preferably two amino acid sequences, of the recombinant proteins, mutants or fragments thereof. VLP comprises or consists of more than one amino acid sequence is referred, in this application, as mosaic VLP.

The term "fragment of a recombinant protein" or the term "fragment of a coat protein", as used herein, is defined as a polypeptide, which is of at least 70%, preferably at least 80%, more preferably at least 90%, even more preferably at least 95% the length of the wild-type recombinant protein, or coat protein, respectively and which preferably retains the capability of forming VLP. Preferably the fragment is obtained by at least one internal deletion, at least one truncation or at least one combination thereof. The term "fragment of a recombinant protein" or "fragment of a coat protein" shall further encompass polypeptide, which has at least 80%, preferably 90%, even more preferably 95% amino acid sequence identity with the "fragment of a recombinant protein" or "fragment of a coat protein", respectively, as defined above and which is preferably capable of assembling into a virus-like particle.

The term "mutant recombinant protein" or the term "mutant of a recombinant protein" as interchangeably used in this invention, or the term "mutant coat protein" or the term "mutant of a coat protein", as interchangeably used in this invention, refers to a polypeptide having an amino acid sequence derived from the wild type recombinant protein, or coat protein, respectively, wherein the amino acid sequence is at least 80%, preferably at least 85%, 90%, 95%, 97%, or 99% identical to the wild type sequence and preferably retains the ability to assemble into a VLP.

Assembly of the fragment or mutant of recombinant protein or coat protein into a VLP may be tested, as one skilled in the art would appreciate by expressing the protein in *E. coli*, optionally purifying the capsids by gel filtration from cell lysate, and analysing the capsid formation in an immunodiffusion assay (Ouchterlony test) or by Electron Microscopy (EM) (Kozlovska, T. M. et al., *Gene* 137:133-37 (1993)). Immunodiffusion assays and EM may be directly performed on cell lysate.

In one preferred embodiment, the virus-like particle of the invention is of Hepatitis B virus. The preparation of Hepatitis B virus-like particles have been disclosed, inter alia, in WO 00/32227, WO 01/85208 and in WO 01/056905. All three documents are explicitly incorporated herein by way of reference. Other variants of HBcAg suitable for use in the practice of the present invention have been disclosed in page 34-39 WO 01/056905.

In one further preferred embodiments of the invention, a lysine residue is introduced into the HBcAg polypeptide, to mediate the linking of GIP of the invention to the VLP of HBcAg. In preferred embodiments, VLPs and compositions of the invention are prepared using a HBcAg comprising, or alternatively consisting of, amino acids 1-144, or 1-149, 1-185 of SEQ ID NO:20, which is modified so that the amino acids at positions 79 and 80 are replaced with a peptide having the amino acid sequence of Gly-Gly-Lys-Gly-Gly. This modification changes the SEQ ID NO:20 to SEQ ID NO:21. In further preferred embodiments, the cysteine residues at positions 48 and 110 of SEQ ID NO:21, or its corresponding fragments, preferably 1-144 or 1-149, are mutated to serine. The invention further includes compositions comprising Hepatitis B core protein mutants having above noted corresponding amino acid alterations. The invention further includes compositions and vaccines, respectively, comprising HBcAg polypeptides which comprise, or alternatively consist of, amino acid sequences which are at least 80%, 85%, 90%, 95%, 97% or 99% identical to SEQ ID NO:21.

In another embodiment of the invention, the virus-like particle is a recombinant alphavirus, and more specifically, a recombinant Sindbis virus. Alphaviruses are positive stranded RNA viruses that replicate their genomic RNA entirely in the cytoplasm of the infected cell without a DNA intermediate (Strauss, J. and Strauss, E., Microbiol. Rev. 58:491-562 (1994)). Several members of the alphavirus family, Sindbis (Schlesinger, S., Trends Biotechnol. 11:18-22 (1993)), Semliki Forest Virus (SFV) (Liljeström, P. & Garoff, H., Bio/Technology 9:1356-1361 (1991)) and others (Davis, N. L. et al., Virology 171:189-204 (1989)), have received considerable attention for use as virus-based expression vectors for a variety of different proteins (Lundstrom, K., Curr. Opin. Biotechnol. 8:578-582 (1997)) and as candidates for vaccine development.

In preferred embodiments of the invention, the virus-like particle of the invention comprises, consists essentially of, or alternatively consists of, recombinant coat proteins, mutants or fragments thereof, of a RNA-phage. Preferably, the RNA-phage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; l) bacteriophage PP7 and m) bacteriophage AP205.

In one preferred embodiment of the invention, the composition comprises coat protein, mutants or fragments thereof, of RNA phages, wherein the coat protein has amino acid sequence selected from the group consisting of: (a) SEQ ID NO:1, referring to Qβ CP; (b) a mixture of SEQ ID NO:1 and SEQ ID NO:2 (referring to Qβ A1 protein); (c) SEQ ID NO:3; (d) SEQ ID NO:4; (e) SEQ ID NO:5; (f) SEQ ID NO:6, (g) a mixture of SEQ ID NO:6 and SEQ ID NO:7; (h) SEQ ID NO:8; (i) SEQ ID NO:9; (j) SEQ ID NO:10; (k) SEQ ID NO:11; (l) SEQ ID NO:12; (m) SEQ ID NO:13; and (n) SEQ ID NO:14. Generally the coat protein mentioned above is capable of assembly into VLP with or without the presence of the N-terminal methionine.

In one preferred embodiment of the invention, the VLP is a mosaic VLP comprising or alternatively consisting of more than one amino acid sequence, preferably two amino acid sequences, of coat proteins, mutants or fragments thereof, of a RNA phage.

In one very preferred embodiment, the VLP comprises or alternatively consists of two different coat proteins of a RNA phage, said two coat proteins have an amino acid sequence of SEQ ID NO: 1 and SEQ ID NO:2, or of SEQ ID NO:6 and SEQ ID NO:7.

In preferred embodiments of the present invention, the virus-like particle of the invention comprises, or alternatively consists essentially of, or alternatively consists of recombinant coat proteins, mutants or fragments thereof, of the RNA-bacteriophage Qβ, fr, AP205 or GA.

In one preferred embodiment, the VLP of the invention is a VLP of RNA-phage Qβ. The capsid or virus-like particle of Qβ showed an icosahedral phage-like capsid structure with a diameter of 25 nm and T=3 quasi symmetry. The capsid contains 180 copies of the coat protein, which are linked in covalent pentamers and hexamers by disulfide bridges (Golmohammadi, R. et al., Structure 4:543-5554 (1996)), leading to a remarkable stability of the Qβ capsid. Capsids or VLPs made from recombinant Qβ coat protein may contain, however, subunits not linked via disulfide bonds to other subunits within the capsid, or incompletely linked. The capsid or VLP of Qβ shows unusual resistance to organic solvents and denaturing agents. Surprisingly, we have observed that DMSO and acetonitrile concentrations as high as 30%, and guanidinium concentrations as high as 1 M do not affect the stability of the capsid. The high stability of the capsid or VLP of Qβ is an advantageous feature, in particular, for its use in immunization and vaccination of mammals and humans in accordance of the present invention.

Further preferred virus-like particles of RNA-phages, in particular of Qβ and fr in accordance of this invention are disclosed in WO 02/056905, the disclosure of which is herewith incorporated by reference in its entirety. Particular example 18 of WO 02/056905 gave detailed description of preparation of VLP particles from Qβ.

In another preferred embodiment, the VLP of the invention is a VLP of RNA phage AP205. Assembly-competent mutant forms of AP205 VLPs, including AP205 coat protein with the substitution of proline at amino acid 5 to threonine, may also be used in the practice of the invention and leads to other preferred embodiments of the invention. WO 2004/007538 describes, in particular in Example 1 and Example 2, how to obtain VLP comprising AP205 coat proteins, and hereby in particular the expression and the purification thereto. WO 2004/007538 is incorporated herein by way of reference. AP205 VLPs are highly immunogenic, and can be linked with GIP of the invention to typically and preferably generate vaccine constructs displaying the GIP of the invention oriented in a repetitive manner. High antibody titer is elicited against the so displayed GIP of the inventions showing that linked GIP of the inventions are accessible for interacting with antibody molecules and are immunogenic.

In one preferred embodiment, the VLP of the invention comprises or consists of a mutant coat protein of a virus, preferably a RNA phage, wherein the mutant coat protein has been modified by removal of at least one lysine residue by way of substitution and/or by way of deletion. In another preferred embodiment, the VLP of the invention comprises or consists of a mutant coat protein of a virus, preferably a RNA phage, wherein the mutant coat protein has been modified by addition of at least one lysine residue by way of substitution and/or by way of insertion. In one very preferred embodiment, the mutant coat protein is of RNA phage Qβ, wherein at least one, or alternatively at least two, lysine residue have been removed by way of substitution or by way of deletion. In an alternative very preferred embodiment, the mutant coat protein is of RNA phage Qβ, wherein at least one, or alternatively at least two, lysine residue have been added by way of substitution or by way of insertion. In one further preferred embodiment, the mutant coat protein of RNA phage Qβ has an amino acid sequence selected from any one of SEQ ID NO:15-19. The deletion, substitution or addition of at least one lysine residue allows varying the degree of coupling, i.e. the amount of GIP of the invention per subunits of the VLP of a virus, preferably of an RNA-phages, in particular, to match and tailor the requirements of the vaccine.

In one preferred embodiment, the compositions and vaccines of the invention have an antigen density being from 0.5 to 4.0. The term "antigen density", as used herein, refers to the average number of GIP of the invention which is linked per subunit, preferably per coat protein, of the VLP, and hereby preferably of the VLP of a RNA phage. Thus, this value is calculated as an average over all the subunits or monomers of the VLP, preferably of the VLP of the RNA-phage, in the composition or vaccines of the invention.

In another preferred embodiment of the present invention, the virus-like particle comprises, or alternatively consists essentially of, or alternatively consists of mutant coat protein of Qβ, or mutants or fragments thereof, and the corresponding A1 protein. In a further preferred embodiment, the virus-like particle comprises, or alternatively consists essentially of, or alternatively consists of mutant coat protein with amino acid sequence SEQ ID NO:15, 16, 17, 18, or 19 and the corresponding A1 protein.

In yet another preferred embodiment of the present invention, the virus-like particle comprises, or alternatively consists essentially of, or alternatively consists of a mixture of recombinant coat proteins, or fragments thereof, of the RNA-phage Qβ, AP205, fr or GA and of recombinant mutant coat proteins, or fragments thereof, of the RNA-phage Qβ, AP205, fr or GA.

Assembly-competent mutant forms of AP205 VLPs, including AP205 coat protein with the substitution of proline at amino acid 5 to threonine, asparigine at amino acid 14 to aspartic acid, may also be used in the practice of the invention and leads to other preferred embodiments of the invention. The cloning of the AP205Pro-5-Thr and the purification of the VLPs are disclosed in WO 2004/007538, and therein, in particular within Example 1 and Example 2. The disclosure of WO 2004/007538, and, in particular, Example 1 and Example 2 thereof is explicitly incorporated herein by way of reference.

Further RNA phage coat proteins have also been shown to self-assemble upon expression in a bacterial host (Kastelein, R A. et al., Gene 23:245-254 (1983), Kozlovskaya, T M. et al., Dokl. Akad. Nauk SSSR 287:452-455 (1986), Adhin, M R. et al., Virology 170:238-242 (1989), Priano, C. et al., J. Mol. Biol. 249:283-297 (1995)). In particular the biological and biochemical properties of GA (Ni, C Z., et al., Protein Sci. 5:2485-2493 (1996), Tars, K et al., J. Mol. Biol. 271:759-773 (1997)) and of fr (Pushko P. et al., Prot. Eng. 6:883-891 (1993), Liljas, L et al. J. Mol. Biol. 244:279-290, (1994)) have been disclosed. The crystal structure of several RNA bacteriophages has been determined (Golmohammadi, R. et al., Structure 4:543-554 (1996)). Using such information, surface exposed residues can be identified and, thus, RNA-phage coat proteins can be modified such that one or more reactive amino acid residues can be inserted by way of insertion or substitution. Another advantage of the VLPs derived from RNA phages is their high expression yield in bacteria that allows production of large quantities of material at affordable cost.

In one preferred embodiment, the composition of the invention comprises at least one antigen, wherein said at least one antigen is a GIP protein or a GIP fragment. In one preferred embodiment, the GIP protein or the GIP fragment is selected from the group consisting of: (a) human GIP protein or GIP fragment; (b) bovine GIP protein or GIP fragment; (c) sheep GIP protein or GIP fragment; (d) dog GIP protein or GIP fragment; (e) feline GIP protein or GIP fragment; (f) mouse GIP protein or GIP fragment; (g) pig GIP protein or GIP fragment; (h) chicken protein or GIP fragment, (i) horse GIP protein or GIP fragment; and (g) rat GIP protein or GIP fragment.

In one preferred embodiment, the at least one antigen is a GIP protein. In a further preferred embodiment, the GIP protein comprises, consists essentially of, or consists of an amino acid sequence selected from the group consisting of: (a) SEQ ID NO:22; (b) SEQ ID NO:23; (c) SEQ ID NO:24; (d) SEQ ID NO:25; (e) SEQ ID NO:26; (f) SEQ ID NO:63; (g) the GIP corresponding orthologs from any other animal; and (h) an amino acid sequence which is at least 80%, or preferably at least 85%, more preferably at least 90%, or most preferably at least 95% identical with any of SEQ ID NO: 22-26 or with SEQ ID NO:63.

In one preferred embodiment, the GIP protein comprises, consists essentially of, or consists of an amino acid sequence, wherein at most 7, preferably 6, 5, 4, more preferably at most 3, 2 or 1 amino acids are deleted, inserted or substituted, preferably by conservative substitutions as compared to the amino acid sequence selected from the group of: (a) SEQ ID NO:22; (b) SEQ ID NO:23; (c) SEQ ID NO:24; (d) SEQ ID NO:25; and (e) SEQ ID NO:26.

In one preferred embodiment, the at least one antigen is a GIP fragment, wherein said GIP fragment comprises or alternatively consists of at least one antigenic site.

Methods to determine antigenic site(s) of a protein are known to the skilled person in the art. PCT/EP2005/004980, has elaborated some of these methods from the first paragraph of page 26 to the fourth paragraph of page 27 therein, and these specific disclosures are incorporated herein by reference. It is to be noted that these methods are generally applicable to other polypeptide antigens, and therefore are not restricted to IL-23 p19 as disclosed in PCT/EP2005/004980.

In a preferred embodiment of the present invention, the GIP fragment comprises, or alternatively or preferably consists of, at least 5 to 12 contiguous amino acids of a GIP protein as defined herein. In a further preferred embodiment, the GIP fragment is selected from the amino part of GIP. The amino part of GIP, as used herein, refers to the first 18, preferably 15 amino acid sequence of GIP of SEQ ID NO:22 or the corresponding orthologs from any other animal.

In one preferred embodiment, the GIP fragment comprises, consists essentially of, or consists of amino acid sequence 7-10 (SEQ ID NO:64), preferably 4-10 (SEQ ID NO:67), preferably 4-13 (SEQ ID NO:32), preferably 1-10 (SEQ ID NO:29), preferably 4-11 (SEQ ID NO:45), preferably 7-15 (SEQ ID NO:65), more preferably 4-15 (SEQ ID NO:66), even more preferably 1-15 (SEQ ID NO:27), of the SEQ ID NO: 22 or the GIP corresponding orthologs from any other animal.

In one preferred embodiment, the GIP fragment comprises, consists essentially of, or consists of amino acid sequence 7-10 (SEQ ID NO:64), preferably 4-10 (SEQ ID NO:67), preferably 4-13 (SEQ ID NO:32), preferably 1-10 (SEQ ID NO:29), preferably 4-11 (SEQ ID NO:45), preferably 7-15 (SEQ ID NO:65), more preferably 4-15 (SEQ ID NO:66), even more preferably 1-15 (SEQ ID NO:27), of the SEQ ID NO: 22 or the GIP corresponding orthologs from any other animal, wherein one amino acid of the 7-10 sequence or wherein 3, preferably 2, even more preferably 1 amino acid from 4-10, 4-13, 1-10, 4-11, 4-15, 7-15 and 1-15, amino acid sequence, have/has been mutated, preferably by deletion, insertion and/or substitution, more preferably by conservative substitutions. Conservative substitutions, as understood by a skilled person in the art, include isosteric substitutions, substitutions where the charged, polar, aromatic, aliphatic or hydrophobic nature of the amino acid is maintained. Typical conservative substitutions are substitutions between amino acids within one of the following groups: Gly, Ala; Val, Ile, Leu; Asp, Glu; Asn, Gln; Ser, Thr, Cys; Lys, Arg; and Phe and Tyr.

In one further preferred embodiment, the GIP fragment comprises, consists essentially of, or consists of an amino acid sequence selected from the group consisting of: (a) SEQ ID NO: 27; (b) SEQ ID NO: 29; (c) SEQ ID NO:32; (d) SEQ ID NO:45; and (e) an amino acid sequence which is at least 80%, or preferably at least 85%, more preferably at least 90%, or most preferably at least 95% identical with SEQ ID NO: 27, 29, 32, or 45.

In one preferred embodiment, the GIP fragment comprises, consists essentially of, or consists of amino acids 20-23, preferably 19-25, more preferably 16-30 of the SEQ ID NO: 22-26 or of SEQ ID NO:63 or the GIP sequence of the corresponding orthologs from any animal. In a further preferred embodiment, the GIP fragment comprises, consists essentially of, or consists of an amino acid sequence selected from the group consisting of: (a) SEQ ID NO: 31; (b) SEQ ID NO:43; and (e) an amino acid sequence which is at least 80%, or preferably at least 85%, more preferably at least 90%, or most preferably at least 95% identical with SEQ ID NO: 31 or 43. In one further preferred embodiment, the GIP fragment comprises, consists essentially of, or consists of amino acid 20-23, preferably 19-25, more preferably 16-30 of the SEQ ID NO: 22-26 or of SEQ ID NO:63 or the GIP sequence of the corresponding orthologs from any other animal, wherein one amino acid of the 20-23 sequence or wherein 3, preferably 2, even more preferably 1 amino acid from 19-25, preferably 16-30 amino acid sequence, have/has been mutated, preferably by deletion, insertion and/or substitution, more preferably by conservative substitutions.

In one preferred embodiment, the GIP fragment comprises, consists essentially of, or consists of amino acid 31-34, preferably 30-34, more preferably 28-34, more preferably 30-37, more preferably 28-37, more preferably 31-42, more preferably 28-42 of the SEQ ID NO: 22-26 or of SEQ ID NO:63 or the GIP sequence of the corresponding orthologs from any other animal. In a further preferred embodiment, the GIP fragment comprises, consists essentially of, or consists of an amino acid sequence selected from the group consisting of: (a) SEQ ID NO:28; (b) SEQ ID NO:44; (c) SEQ ID NO:68; and (d) an amino acid sequence which is at least 80%, or preferably at least 85%, more preferably at least 90%, or most preferably at least 95% identical with SEQ ID NO: 28, 44 or 68. In one preferred embodiment, the GIP fragment comprises consists essentially of, or consists of amino acid 31-34, preferably 30-34, more preferably 28-34, more preferably 26-34, more preferably 30-37, more preferably 28-37, more preferably 26-37, even more preferably 31-42, more preferably 28-42, more preferably 26-42, of the SEQ ID NO: 22-26 or of SEQ ID NO:63 or the GIP sequence of the corresponding orthologs from any other animal, wherein one amino acid of the 31-34 or 30-34 sequence or wherein 3, preferably 2, even more preferably 1 amino acid from 28-34, 30-37, 28-37, 31-42, or 28-42 sequence, have/has been mutated, preferably by deletion, insertion and/or substitution, more preferably by conservative substitutions.

In one preferred embodiment, the GIP fragment or the GIP protein further comprises a stretch of hydrophilic amino acids fused to the GIP fragment or the GIP protein as described above. A stretch of hydrophilic amino acids as used herein, refers to a stretch of amino acids, in which at least 60%, preferably at least 70%, more preferably at least 80%, still more preferably at least 90% amino acids therein are hydrophilic amino acids. In a preferred embodiment, the stretch of amino acids consists of at most 7, preferably 6, 5, 4, more preferably 3, more preferably 2 or one amino acids. Addition of hydrophilic amino acids increases the solubility of the GIP fragment or the GIP protein. In one further preferred embodiment, the hydrophilic amino acids are glycine, serine, threonine and the charged amino acids. In one further preferred embodiment, the charged amino acids are lysine, arginine, aspartic acid, glutamic acid. In one preferred embodiment, the stretch of amino acids comprises or consists of the amino acid sequence DD, KK, RR, DE, ED; EE, KR, RK.

In one preferred embodiment, the GIP fragment comprises, consists essentially of, or consists of the amino acid sequence selected from the group consisting of: (a) amino acid 1-12 of SEQ ID NO:22 with DD or KK added at the C terminus; (b) amino acid 1-13 of SEQ ID NO:22 with DD or KK added at the C-terminus; (c) amino acid 1-14 of SEQ ID NO:22 with DD or KK added at the C-terminus (SEQ ID NO:69 and 70); (d) amino acid 1-15 of SEQ ID NO:22 with DD or KK added at the C-terminus (SEQ ID NO:71 and 72) and (e) amino acid 1-11 of SEQ ID NO:22 with DD or KK added at the C terminus.

In one embodiment, the at least one antigen of the invention comprises at least two GIP fragments, preferably two GIP fragments. In one preferred embodiment, the two GIP fragments are two different GIP fragments. In one preferred embodiment, the two GIP fragments are fused into one polypeptide. In one embodiment, the two GIP fragment are fused directly. In another embodiment, the two GIP fragments are fused through a spacer sequence.

In one preferred embodiment of the invention, the VLP with at least one first attachment site is linked to the GIP of the invention with at least one second attachment site via at least one peptide bond. Gene encoding GIP of the invention, preferably GIP fragment, more preferably a fragment not longer than 50 amino acids, even more preferably less than 30 amino acids, is in-frame ligated, either internally or preferably to the N- or the C-terminus to the gene encoding the coat protein of the VLP. Embodiments of fusing antigen of the invention to coat protein, mutants or fragments thereof, to a virus, preferably to an RNA phage, have been disclosed in WO 2004/009124 page 62 line 20 to page 68 line 17 and herein are incorporated by way of reference. The fusion protein shall preferably retain the ability of assembly into a VLP upon expression which can be examined by electromicroscopy.

Flanking amino acid residues may be added to increase the distance between the coat protein and foreign epitope. Glycine and serine residues are particularly favored amino acids to be used in the flanking sequences. Such a flanking sequence confers additional flexibility, which may diminish the potential destabilizing effect of fusing a foreign sequence into the sequence of a VLP subunit and diminish the interference with the assembly by the presence of the foreign epitope.

In another preferred embodiment, GIP of the invention, preferably GIP fragments, even more preferably GIP fragment with amino acid sequenced SEQ ID NO: 27-32, SEQ ID NO: 43-45, SEQ ID NO:66 or 68 is fused to either the N- or the C-terminus of a coat protein, mutants or fragments thereof, of RNA phage AP205. In one further preferred embodiment, the fusion protein further comprises a spacer, wherein said spacer is positioned between the coat protein, fragments or mutants thereof, of AP205 and the GIP of the invention.

In one preferred embodiment of the present invention, the composition comprises or alternatively consists essentially of a virus-like particle with at least one first attachment site linked to at least one GIP of the invention with at least one second attachment site via at least one covalent bond, preferably the covalent bond is a non-peptide bond. In a preferred embodiment of the present invention, the first attachment site comprises, or preferably is, an amino group, preferably the amino group of a lysine residue. In another preferred embodiment of the present invention, the second attachment site comprises, or preferably is, a sulfhydryl group, preferably a sulfhydryl group of a cysteine. In another preferred embodiment of the present invention, the second attachment site comprises, or preferably is a maleimido group that that is associated, preferably, covalently associated with the at least one antigen.

In a very preferred embodiment of the invention, at least one first attachment site comprises, or preferably is, an amino group, preferably an amino group of a lysine residue and the at least one second attachment site comprises, or preferably is, a sulfhydryl group, preferably a sulfhydryl group of a cysteine.

In one preferred embodiment of the invention, the GIP of the invention is linked to the VLP by way of chemical cross-linking, typically and preferably by using a heterobifunctional cross-linker. In preferred embodiments, the heterobifunctional cross-linker contains a functional group which can react with the preferred first attachment sites, preferably with the amino group, more preferably with the amino groups of lysine residue(s) of the VLP, and a further functional group which can react with the preferred second attachment site, i.e. a sulfhydryl group, preferably of cysteine(s) residue inherent of, or artificially added to the GIP of the invention, and optionally also made available for reaction by reduction. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company, and having one functional group reactive towards amino groups and one functional group reactive towards sulfhydryl groups. The above mentioned cross-linkers all lead to formation of an amide bond after reaction with the amino group and a thioether linkage with the sulfhydryl groups. Another class of cross-linkers suitable in the practice of the invention is characterized by the introduction of a disulfide linkage between the GIP of the invention and the VLP upon coupling. Preferred cross-linkers belonging to this class include, for example, SPDP and Sulfo-LC-SPDP (Pierce).

In a preferred embodiment, the composition of the invention further comprises a linker. Engineering of a second attachment site onto the GIP of the invention is achieved by the association of a linker, preferably containing at least one amino acid suitable as second attachment site, according to the disclosures of this invention. Therefore, in a preferred embodiment of the present invention, a linker is associated to the GIP of the invention by way of at least one covalent bond, preferably, by at least one, typically one peptide bond. Preferably, the linker comprises, or alternatively consists of, the second attachment site. In a further preferred embodiment, the linker comprises a sulfhydryl group, preferably of a cysteine residue. In another preferred embodiment, the amino acid linker is a cysteine residue.

The selection of a linker will be dependent on the nature of the GIP of the invention, on its biochemical properties, such as pI, charge distribution and glycosylation. In general, flexible amino acid linkers are favored. In a further preferred embodiment of the present invention, the linker consists of amino acids, wherein further preferably the linker consists of at most 25, preferably at most 20, more preferably at most 15 amino acids. Preferred embodiments of the linker are selected from the group consisting of: (a) CGG or CG/GC; (b) N-terminal gamma 1-linker (e.g. CGDKTHTSPP, SEQ ID NO:48); (c) N-terminal gamma 3-linker (e.g. CGGPKPSTP-PGSSGGAP, SEQ ID NO: 59); (d) Ig hinge regions; (e) N-terminal glycine linkers (e.g. GCGGGG, SEQ ID NO:49); (f) (G)kC(G)n with n=0-12 and k=0-5; (g) N-terminal glycine-serine linkers ((GGGGS)n, n=1-3 with one further cysteine (for example SEQ ID NO:50, which corresponds to an embodiment wherein n=1); (h) (G)kC(G)m(S)l(GGGGS)n with n=0-3, k=0-5, m=0-10, l=0-2 (for example SEQ ID NO:51, which corresponds to an embodiment wherein n=1, k=1, l=1 and m=1); (i) GGC; (k) GGC-NH2; (l) C-terminal gamma 1-linker (e.g. DKTHTSPPCG, SEQ ID NO:52); (m) C-terminal gamma 3-linker (e.g. PKPSTPPGSSGGAPG-GCG, SEQ ID NO:53); (n) C-terminal glycine linkers (GGGGCG, SEQ ID NO:54); (o) (G)nC(G)k with n=0-12 and k=0-5; (p) C-terminal glycine-serine linkers ((SGGGG)n n=1-3 with one further cysteine (for example SEQ ID NO:55, which corresponds to an embodiment wherein n=1); (q) (G)m (S)l(GGGGS)n(G)oC(G)k with n=0-3, k=0-5, m=0-10, l=0-2, and o=0-8 (for example SEQ ID NO:56, which corresponds to an embodiment wherein n=1, k=1, l=1, o=1 and m=1). In a further preferred embodiment the linker is added to the N-terminus of GIP of the invention. In another preferred embodiment of the invention, the linker is added to the C-terminus of GIP of the invention.

Preferred linkers according to this invention are glycine linkers (G)n further containing a cysteine residue as second attachment site, such as N-terminal glycine linker (GCGGGG) and C-terminal glycine linker (GGGGCG). Further preferred embodiments are C-terminal glycine-lysine linker (GGKKGC, SEQ ID NO:57) and N-terminal glycine-lysine linker (CGKKGG, SEQ ID NO:58), GGCG a GGC or GGC-NH2 ("NH2" stands for amidation) linkers at the C-terminus of the peptide or CGG at its N-terminus. In general, glycine residues will be inserted between bulky amino acids and the cysteine to be used as second attachment site, to avoid potential steric hindrance of the bulkier amino acid in the coupling reaction.

In one preferred embodiment, the linker sequence is GC, preferably GC is associated to the C-terminal of GIP protein or GIP fragment, preferably to the SEQ ID NO:22-27, 29, 31-32, 43 or 45. In another preferred embodiment, the linker sequence is CG, preferably CG is fused to the N-terminal of GIP protein or GIP fragment, preferably to the SEQ ID NO:28, 44 or 68.

The cysteine residue(s) served as the second attachment site, either inherent of or added to the GIP of the invention, has to be in reduced state to react with the hetero-bifunctional cross-linker on the activated carrier, that is a free cysteine or a cysteine residue with a free sulfhydryl group has to be available.

Linking of the GIP of the invention to the VLP by using a hetero-bifunctional cross-linker according to the preferred methods described above, allows coupling of the GIP of the invention to the VLP in an oriented fashion. Other methods of linking the GIP of the invention to the VLP include methods wherein the GIP of the invention is cross-linked to the VLP, using the carbodiimide EDC, and NHS. The GIP of the invention may also be first thiolated through reaction, for example with SATA, SATP or iminothiolane. The GIP of the invention, after deprotection if required, may then be coupled to the VLP as follows. After separation of the excess thiolation reagent, the GIP of the invention is reacted with the VLP, previously activated with a hetero-bifunctional cross-linker comprising a cysteine reactive moiety, and therefore displaying at least one or several functional groups reactive towards cysteine residues, to which the thiolated GIP of the invention can react, such as described above. Optionally, low amounts of a reducing agent are included in the reaction mixture. In further methods, the GIP of the invention is attached to the VLP, using a homo-bifunctional cross-linker such as glutaraldehyde, DSG, BM[PEO]4, BS3, (Pierce) or other known homo-bifunctional cross-linkers with functional groups reactive towards amine groups or carboxyl groups of the VLP.

In one preferred embodiment, the first attachment site comprises, or preferably is, a sulfhydryl group, even more preferable a sulfhydryl group of a cysteine naturally or artificially added to the coat protein comprised, or alternatively consisted essentially of by the VLP. The second attachment site is the maleimido group of a linker, such as MBS (m-Maleimidobenzoyl-N-hydroxysuccinimide ester) or SMPH (Succinimidyl-6-[β-maleimidopropionamido]hexanoate), which is chemically associated with the antigen, preferably covalently associated with the antigen, more preferably covalently associated with an amino group of the antigen, even more preferably covalently associated by a NHS-ester group of the linker with the amino group of the N-terminus amino acid of the antigen. In one preferred embodiment, the at least one antigen, preferably no more than 50, even more preferably no more than 30 amino acids, even more preferably GIP protein or GIP fragment of SEQ ID NO:22-27, 29, 31-32, 43 or 45 is preferably chemically synthesized and the maleimido group is preferably associated to the amino group of the N-terminus amino acid. The first attachment site and the second attachment site are linked through a thio-ether bond.

In one alternatively preferred embodiment, the first attachment site comprises, or preferably is, an amino group, preferably an amino group of a lysine naturally occurring or artificially added to the coat protein comprised or alternatively consisted essentially of by the VLP. The second attachment site is the maleimido group of a linker as elaborated in the above paragraph. The amino group of the VLP is derivatized by a hetero-bifunctional crosslinker, such as N-Succinimidyl-S-acetylthioacetate (SATA) or 2-Iminothiolane, into a sulfhydryl group, which is then reactive to the maleimido group of the linker.

Preferred linkers comprising at least one maleimido group are, for example, SMPH, Sulfo-MBS. Further preferred linkers are Sulfo-EMCS, Sulfo-GMBS, Sulfo-SIAB, Sulfo-SMPB, Sulfo-SMCC, SVSB, SIA and other cross-linkers available, for example, from the Pierce Chemical Company, and having one functional group reactive towards amino groups and one functional group reactive towards sulfhydryl groups.

In other embodiments of the present invention, the composition comprises or alternatively consists essentially of a virus-like particle linked to GIP of the invention via chemical interactions, wherein at least one of these interactions is not a covalent bond. For example, linking of the VLP to the GIP of the invention can be effected by biotinylating the VLP and expressing the GIP of the invention as a streptavidin-fusion protein. Other binding pairs, such as ligand-receptor, antigen-antibody, can also be used as coupling reagent in a similar manner as biotin-avidin.

U.S. Pat. No. 5,698,424 describes a modified coat protein of bacteriophage MS-2 capable of forming a capsid, wherein the coat protein is modified by an insertion of a cysteine residue into the N-terminal hairpin region, and by replacement of each of the cysteine residues located external to the N-terminal hairpin region by a non-cysteine amino acid residue. The inserted cysteine may then be linked directly to a desired molecular species to be presented such as an epitope or an antigenic protein.

We note, however, that the presence of an exposed free cysteine residue in the capsid may lead to oligomerization of capsids by way of disulfide bridge formation. Moreover, attachment between capsids and antigenic proteins by way of disulfide bonds are labile, in particular, to sulfhydryl-moiety containing molecules, and are, furthermore, less stable in serum than, for example, thioether attachments (Martin F J. and Papahadjopoulos D. (1982) Irreversible Coupling of Immunoglobulin Fragments to Preformed Vesicles. J. Biol. Chem. 257: 286-288).

Therefore, in a further very preferred embodiment, the linkage of the VLP and the at least one antigen does not comprise a disulfide bond. Further preferred hereby, the at least one second attachment comprise, or preferably is, a sulfhydryl group. Moreover, in again a very preferred embodiment of the invention, the linkage of the VLP and the at least one antigen does not comprise a sulphur-sulphur bond. In a further very preferred embodiment, said at least one first attachment site is not or does not comprise a sulfhydryl group of a cysteine. In again a further very preferred embodiment, said at least one first attachment site is not or does not comprise a sulfhydryl group.

In one preferred embodiment of the invention, the VLP is recombinantly produced in a host, and wherein the VLP is essentially free of host RNA, preferably host nucleic acids or wherein the VLP is essentially free of host DNA, preferably host nucleic acids. In one preferred embodiment, the VLP of an RNA phage is recombinantly produced in a host, and wherein the VLP of an RNA phage is essentially free of host RNA, preferably host nucleic acids.

In one further preferred embodiment, the composition further comprises at least one polyanionic macromolecule bound to, preferably packaged inside or enclosed in, the VLP. In a still further preferred embodiment, the polyanionic macromolecule is polyglutamic acid and/or polyaspartic acid. In one preferred embodiment, the VLP is of an RNA phage. Reducing or eliminating the amount of host RNA, preferably host nucleic acids, minimizes or reduces unwanted T cell responses, such as inflammatory T cell responses and cytotoxic T cell responses, and other unwanted side effects, such as fever, while maintaining strong antibody response specifically against GIP.

Essentially free of host RNA (or DNA), preferably host nucleic acids: The term "essentially free of host RNA (or DNA), preferably host nucleic acids" as used herein, refers to the amount of host RNA (or DNA), preferably host nucleic acids, comprised by the VLP, which is typically and preferably less than 30 µg, preferably less than 20 µg, more preferably less than 10 µg, even more preferably less than 8 µg, even more preferably less than 6 µg, even more preferably less than 4 µg, most preferably less than 2 µg, per mg of the VLP. Host, as used within the afore-mentioned context, refers to the host in which the VLP is recombinantly produced. Conventional methods of determining the amount of RNA (or DNA), preferably nucleic acids, are known to the skilled person in the art. The typical and preferred method to determine the amount of RNA, preferably nucleic acids, in accordance with the present invention is described in Example 17 of the PCT/EP2005/055009 filed on Oct. 5, 2005 by the same assignee. Identical, similar or analogous conditions are, typically and preferably, used for the determination of the amount of RNA (or DNA), preferably nucleic acids, for inventive compositions comprising VLPs other than Qβ. The modifications of the conditions eventually needed are within the knowledge of the skilled person in the art.

The term "polyanionic macromolecule", as used herein, refers to a molecule of high relative molecular mass which comprises repetitive groups of negative charge, the structure of which essentially comprises the multiple repetitions of units derived, actually or conceptually, from molecules of low relative molecular mass.

In one aspect, the invention provides a vaccine composition comprising the composition of the invention. In one preferred embodiment, the GIP of the invention linked to the VLP in the vaccine composition is of animal, preferably mammal or human origin. In further preferred embodiments, the GIP of the invention is of human, bovine, chicken, dog, cat, mouse, rat, pig or horse origin.

In one preferred embodiment, the vaccine composition further comprises at least one adjuvant. The administration of at least one adjuvant may hereby occur prior to, contemporaneously or after the administration of the inventive composition. The term "adjuvant" as used herein refers to non-specific stimulators of the immune response or substances that allow generation of a depot in the host which when combined with the vaccine and pharmaceutical composition, respectively, of the present invention may provide for an even more enhanced immune response. A variety of adjuvants can be used. Examples include complete and incomplete Freund's adjuvant, aluminum hydroxide and modified muramyldipeptide. Further adjuvants are mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette Guerin) and *Corynebacterium parvum*. Such adjuvants are also well known in the art. Further adjuvants that can be administered with the compositions of the invention include, but are not limited to, Monophosphoryl lipid immunomodulator, Adju-Vax 100a, QS-21, QS-18, CRL1005, Aluminum salts (Alum), MF-59, OM-174, OM-197, OM-294, and Virosomal adjuvant technology. The adjuvants can also comprise a mixture of these substances.

In another preferred embodiment, the vaccine composition is devoid of adjuvant.

An advantageous feature of the present invention is the high immunogenicity of the composition, even in the absence of adjuvants. The absence of an adjuvant, furthermore, minimizes the occurrence of unwanted inflammatory T-cell responses representing a safety concern in the vaccination against self antigens. Thus, the administration of the vaccine of the invention to a patient will preferably occur without administering at least one adjuvant to the same patient prior to, contemporaneously or after the administration of the vaccine.

In a further aspect, the present invention provides for the use of a composition comprising (a) a virus-like particle with at least one first attachment site and (b) at least one non-human, preferably a non-human vertebrate GIP of the invention with at least one second attachment site, wherein (a) and (b) are linked through the at least one first and the at least one second attachment, for the manufacture of a medicament for treatment of GIP-related diseases, in particular obesity, in humans. These preferred embodiments comprising at least one non-human GIP of the invention such as, for example, feline, canine, bovine, rat or mouse GIP of the invention, are capable of inducing cross-reactive antibody responses recognizing human GIP.

The invention further discloses a method of immunization comprising administering the vaccine of the present invention to an animal or a human. The animal is preferably a mammal, such as cat, sheep, pig, horse, bovine, dog, rat, mouse and particularly a dog or a cat, preferably a domestic cat. The vaccine may be administered to an animal or a human by various methods known in the art, but will normally be administered by injection, infusion, inhalation, oral administration, or other suitable physical methods. The conjugates may alternatively be administered intramuscularly, intravenously, transmucosally, transdermally, intranasally, intraperitoneally or subcutaneously. Components of conjugates for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Vaccines of the invention are said to be "pharmacologically acceptable" if their administration can be tolerated by a recipient individual. Further, the vaccines of the invention will be administered in a "therapeutically effective amount" (i.e., an amount that produces a desired physiological effect). The nature or type of immune response is not a limiting factor of this disclosure. Without the intention to limit the present invention by the following mechanistic explanation, the inventive vaccine might induce antibodies which bind to GIP and thus reducing its concentration and/or interfering with its physiological or pathological function.

In another aspect, the invention provides a pharmaceutical composition comprising the composition as taught in the present invention and an acceptable pharmaceutical carrier. When vaccine of the invention is administered to an individual, it may be in a form which contains salts, buffers, adjuvants, or other substances which are desirable for improving the efficacy of the conjugate. Examples of materials suitable for use in preparation of pharmaceutical compositions are provided in numerous sources including REMINGTON'S PHARMACEUTICAL SCIENCES (Osol, A, ed., Mack Publishing Co., (1990)).

In one further aspect, the invention provides method of producing the composition of the invention, or the vaccine composition of the invention or the pharmaceutical composition of the invention, wherein the method comprises: (a) providing a VLP with at least one first attachment site; (b) providing at least one antigen, wherein said antigen is a GIP protein, or a GIP fragment, with at least one second attachment site; and (c) linking said VLP to said at least one antigen through said at least one first attachment site and said at least one second attachment site to produce said composition.

In a further preferred embodiment, the step of providing a VLP with at least one first attachment site further comprises steps: (a) disassembling said virus-like particle to said coat proteins, mutants or fragments thereof, of said virus, preferably an RNA-bacteriophage; (b) purifying said coat proteins, mutants or fragments thereof; (c) reassembling said purified coat proteins, mutants or fragments thereof, of said virus, preferably an RNA-bacteriophage to a virus-like particle, wherein said virus-like particle is essentially free of host RNA (or DNA), preferably host nucleic acids. In a still further preferred embodiment, the reassembling of said purified coat proteins is effected in the presence of at least one polyanionic macromolecule, preferably polyglutamic acid and/or polyaspartic acid.

In again one aspect, the invention provides compositions which may be used for preventing, treating and/or attenuating diseases or conditions in which GIP exert an important pathological function, in particular obesity.

In a further aspect, the invention provides a kit comprising at least one first composition and at least one second composition, wherein said first composition comprising: (a) a first virus-like particle (VLP) with at least one first attachment site; (b) at least one first antigen with at least one second attachment site, wherein said at least one first antigen is a GIP protein or a GIP fragment and wherein (a) and (b) are linked through said at least one first and said at least one second attachment site; and wherein said second composition comprising: (c) a second virus-like particle (VLP) with at least one first attachment site; (d) at least one second antigen with at least one second attachment site, wherein said at least one second antigen comprises or is a molecule selected from the group consisting of: (i) a ghrelin or a ghrelin peptide; (ii) a nicotine, a cotinine or a nornicotine; and (iii) a second GIP protein or a second GIP fragment, wherein the second GIP protein or GIP fragment is different from the first GIP protein or GIP fragment comprised by the first composition, and wherein (c) and (d) are linked through said at least one first and said at least one second attachment site.

In preferred embodiments, the first composition is the composition of the invention, the first virus-like particle is the virus-like particle of the invention and the first antigen is the at GIP of the invention. Likewise the second virus like particle is the virus like particle of the invention. Thus the feature, the preferred embodiments, the make and use of the first composition, the first virus like particle and the first antigen have been all described and defined in this invention.

In one preferred embodiment, the first VLP and the second VLP are different. In one preferred embodiment, the first VLP and the second VLP are the same. In one preferred embodiment of the invention, the first and/or the second virus-like particle are/is of a RNA phage, wherein preferably said RNA phage is RNA phage Qβ, fr, GA or AP205. In one preferred embodiment, the first virus-like particle and/or the second virus-like particle comprise(s) or consist(s) of recombinant proteins, mutants or fragments thereof, of a RNA-phage, wherein preferably said RNA phage is RNA phage Qβ, fr, GA or AP205. In one further preferred embodiment, the first and the second VLP are both of RNA phage, preferably of RNA phage Qβ. In one preferred embodiment, the first and/or the second VLP of a virus, preferably of an RNA phage, are/is recombinantly produced in a host and wherein said first and/or second VLP are/is essentially free of host RNA, preferably free of host nucleic acids.

In one preferred embodiment, the ghrelin or ghrelin peptide is selected from a group consisting of: (a) human ghrelin or ghrelin peptide; (b) dog ghrelin or ghrelin peptide; (c) cat ghrelin or ghrelin peptide; (d) bovine ghrelin or ghrelin peptide; (e) pig ghrelin or ghrelin peptide; (f) sheep ghrelin or ghrelin peptide; and (g) mouse ghrelin or ghrelin peptide. In one further preferred embodiment, the ghrelin or ghrelin peptide comprises, consists essentially of, or consists of an amino acid sequence selected from the group consisting of: (a) SEQ ID NO: 33; (b) SEQ ID NO:35; (c) SEQ ID NO:40; (d) SEQ ID NO:36; (e) SEQ ID NO:37; (f) SEQ ID NO:38; (g) SEQ ID NO: 46 (GSSFLSPEHQKLQ); and (h) SEQ ID NO: 47 (GSSFLSPEHQKVQ).

The preparation and use of a preferred embodiment of the second composition, wherein said at least one second antigen is ghrelin or a ghrelin peptide have been disclosed in patent application WO 2004/009124 and in WO2005/068639, the two entire disclosures are incorporated herein by way of reference. Further preferred embodiments of the second composition of the present invention are explicitly defined in the claims of WO 2004/009124, and hereby in particular in claims 1 to 31 of WO 2004/009124, as well as in the claims of WO2005/068639, and hereby in particular in claims 1 to 29, which are explicitly incorporated herein by way of reference.

The preparation and use of another preferred embodiment of the second composition, wherein said at least one second antigen comprises or is a nicotine, a cotinine or a nornicotine, have been disclosed in patent application WO 2004/009116 filed by the present assignee. This disclosures is incorporated herein by way of reference. Further preferred embodiments of the second composition of the present invention are explicitly defined in the claims of WO 2004/009116, and hereby in particular in claims 1 to 50 of WO 2004/009116, which are explicitly incorporated herein by way of reference.

In one preferred embodiment, the at least one second antigen is formed from materials selected from the group consisting of: (a) 6-(carboxymethylureido)-(±)-nicotine (CMU-Nic); (b) trans-3'-aminomethylnicotine succinate; (c) O-succinyl-3'-hydroxymethyl-nicotine; (d) Trans-4'-carboxycotinine; (e) N-[1-oxo-6-[(2S)-2-(3-pyridyl)-1-pyrrolidinyl]hexyl]-β-alanine; (f) 4-oxo-4-[[6-[(5S)-2-oxo-5-(3-pyridinyl)-1-pyrrolidinyl]]hexyl]amino]-butanoic acid; (g) (2S)-2-(3-pyridinyl)-1-pyrrolidinebutanoic acid phenylmethyl ester; (h) (2R)-2-(3-pyridinyl)-1-pyrrolidinebutanoic acid phenylmethyl ester; (i) Cotinine 4'-carboxylic acid, N-succinyl-6-amino-(±)-nicotine; (j) 6-(.sigma.-aminocapramido)-(±)-nicotine; (k) 6-(.sigma.-aminocapramido)-(±)-nicotine; (l) 3' aminomethylnicotine; (m) 4' aminomethylnicotine; (n) 5' aminomethylnicotine; (O) 5 aminonicotine; (p) 6 aminonicotine; (q) S-1-(b-aminoethyl) nicotinium chloride; (r) S-1-(b-aminoethyl) cotinium chloride and (s) N-succinyl-6-amino-(±)-nicotine.

In one further preferred embodiment, the second composition comprises O-succinyl-3'-hydroxymethyl-nicotine. In one further preferred embodiment, the second composition comprises O-succinyl-trans-3'-hydroxymethyl-nicotine. In one further preferred embodiment, the second composition comprises O-succinyl-3'-hydroxymethyl-nicotine conjugated to a virus-like particle of a RNA-phage, preferably to a Qβ virus like particle, and hereby preferably to a Qβ virus like particle comprising, or preferably being composed of coat proteins of RNA-phage Qβ.

In one preferred embodiment, the at least one second antigen comprises or is O-succinyl-3'-hydroxymethyl-nicotine. In one further preferred embodiment, the second antigen comprises or preferably is O-succinyl-trans-3'-hydroxymethyl-nicotine. In one preferred embodiment, the second antigen comprises or preferably is trans-3'-hydroxymethyl-nicotine.

In one preferred embodiment, the second attachment site comprised by the second composition contains, or preferably is, an active group selected from the group consisting of: (a) Amine; (b) Amide; (c) Carboxyl; (d) Carbonyl; (e) Sulfhydryl; (f) Hydroxyl; (g) Aldehyde; (h) Diazonium; (i) Alkylhalogenid; (j) Hydrazine; (k) Vinyl; (l) Maleimid; (m) Succinimide; and (n) Hydrazide.

In one preferred embodiment, the association of the first attachment site with the second attachment site through at least one, preferably one, covalent bond is formed by reaction of the O-succinyl moiety of said O-succinyl-3'-hydroxymethyl-nicotine with the first attachment site. In one further preferred embodiment, said association of the first attachment site with the second attachment site through at least one, preferably one, covalent bond is formed by way of amide bond. In one further preferred embodiment, the first attachment site comprises or preferably is an amino group, preferably an amino group of lysine. In one further preferred embodiment, the second attachment site comprises or preferably is a carboxyl group. In one further preferred embodiment, association of the first attachment site with the second attachment site through at least one, preferably one, covalent bond is formed by reaction of the O-succinyl moiety of said O-succinyl-3'-hydroxymethyl-nicotine with an amino group of lysine residue being said first attachment site.

The second composition is preferably formed from succinic acid mono-(1-methyl-2-pyridin-3-yl-pyrrolidin-3-ylmethyl) ester by reacting the carboxyl group of the succinic acid with an amine group of the RNA phage, preferably the amine group of a lysine of the RNA phage.

A preferred way for performing the reaction is by activating the carboxyl group with a carbodiimid, preferably EDC, even more preferably DCC. The activated carboxyl group is either directly covalently linked to RNA phages or is converted to N-hydroxysuccinimid (NHS) ester by addition of N-hydroxysuccinimid (NHS) ester. The NHS ester is either used directly after reaction with the activated carboxyl group or isolated and subsequently reacted with the RNA phage.

Alternative reagents to active carboxyl groups are uronium salts such as HATU (2-(7-Aza-1H-benzotriazole-1-yl)-1,1,3,3-tetramethyluronium hexafluorophosphate) or HBTU (2-(1H-benzotriazole-1-yl)-1,1,3,3-tetramethyluronium hexafluorophosphate). Succinic acid mono-(1-methyl-2-pyridin-3-yl-pyrrolidin-3-ylmethyl) ester will be activated by HATU or HBTA and the corresponding activated carboxyl groups are directly reacted with the amines.

In one preferred embodiment, the at least one second antigen is a GIP protein or a GIP fragment, wherein the second GIP protein or GIP fragment is different from the first GIP protein or GIP fragment comprised by the first composition.

In one preferred embodiment, the second GIP protein or GIP fragment comprises or consists of an amino acid sequence having different chemical modification as compared to the same amino acid sequence comprised or consists of by the first GIP protein or GIP fragment. In one preferred embodiment, the second GIP protein or GIP fragment comprises or consists of an amino acid sequence different from the amino acid sequence comprised or consists of by the first GIP protein or GIP fragment. In one preferred embodiment, the second GIP protein or GIP fragment comprises or consists of at least one different antigenic site as compared to the antigenic site(s) comprised or consists of by the first GIP protein or GIP fragment. In one further preferred embodiment, the second GIP protein or GIP fragment comprises or consists of different antigenic site(s) as compared to the antigenic site(s) comprised or consists of by the first GIP protein or GIP fragment. In one still further preferred embodiment, the first GIP fragment comprises or consists of at least one antigenic site from the amino part of GIP and the second GIP fragment comprises or consists of at least one antigenic site from the carboxyl part of GIP. The carboxyl part of GIP refers to the last 18, preferably 15 amino acids of SEQ ID NO:22-26 or SEQ ID NO:63. In one preferred embodiment, the first GIP fragment comprises or consists of an amino acid sequence as of SEQ ID NO:27 and the second first GIP fragment comprises or consists of an amino acid sequence as of SEQ ID NO:28. The feature, preferred embodiments, the make and use of the different GIP protein or GIP fragment have been all described and defined in this invention.

In one preferred embodiment, the second GIP fragment comprises an amino acid sequence selected from the group consisting of (a) SEQ ID NO: 27; (b) SEQ ID NO: 29; (c) SEQ ID NO:32; (d) SEQ ID NO:45; (e) SEQ ID NO: 28; (f) SEQ ID NO: 31; (g) SEQ ID NO:44; (h) SEQ ID NO:68; and (i) an amino acid sequence which is at least 80%, preferably at least 85%, more preferably at least 90%, or most preferably at least 95% identical with SEQ ID NO: 27-29, 31, 32, 44, 68 or 45.

Except the antigen difference comprised by the first composition and the second composition, the feature and preferred embodiments, the make and use of the second composition is substantially the same as described and defined for the first composition in this invention.

In another further aspect, the present invention provides for a method of treating and/or preventing obesity in an animal or a human comprising administering the at least one first composition and the at least one second composition of the kit to the same animal, preferably to a domestic cat or a dog, or human. The administration of the second composition preferably occurs to the animal or human prior to, contemporaneously or after the administering to the same animal or human the first composition. In one preferred embodiment, the two compositions are preferably administered to the same patient not more than two weeks apart, preferably not more than one week apart, more preferably not more than three days apart, even more preferably not more than 24 hours. In one further preferred embodiment, the two compositions are administered to the same animal or human contemporaneously. Contemporaneously, as used herein, refers to that the two compositions are mixed before the injection to one animal or a human or that the two compositions are administered to the same animal or human in succession. In succession, as used herein, refers to the two compositions are administered to the same animal or human separately but within a not longer than 4 hours interval, preferably no longer than 2 hours, even more preferably not longer than one hour, even more preferably not longer than half hour, still preferably not longer than 10 minutes interval.

In again a preferred embodiment, said first composition and said second composition are administered by the same route, and wherein preferably said route is subcutaneously. In one preferred embodiment, the first composition and the second composition are administered contemporaneously.

In another aspect, the present invention provides a method of preventing and/or treating obesity in an animal or a human comprising administering the vaccine of the invention and a vaccine of VLP-ghrelin, a vaccine of VLP-nicotine, or a vaccine of VLP-a second GIP protein or a second GIP fragment, to the same animal or human. The "vaccine of VLP-ghrelin" comprises the second composition of the invention, wherein the at least antigen is a ghrelin or a ghrelin peptide. In one preferred embodiment, the "vaccine of VLP-ghrelin" further comprises at least one adjuvant. Moreover, the "vaccine of VLP-nicotine" comprises the second composition of the invention, wherein the at least antigen comprises a nicotine, a cotinine or a nornicotine. In one preferred embodiment, the "vaccine of VLP-a second GIP protein or a second GIP fragment" comprises the second composition of the invention, wherein the at least antigen comprises or is a second GIP protein or GIP fragment and wherein the second GIP protein or GIP fragment is different from the first GIP protein or GIP fragment.

For simplicity reason, the vaccine of the invention and the vaccine of the VLP-ghrelin or VLP-nicotine or VLP-a second GIP protein or a second GIP fragment will be referred as "the two vaccines" hereafter.

The administering the vaccine of VLP-ghrelin, the vaccine of VLP-nicotine, or the vaccine of VLP-different GIP protein or GIP fragment preferably occurs to the animal or human prior to, contemporaneously or after the administering to the same animal or human the vaccine of the invention. In one preferred embodiment, the at least one antigen is a GIP protein or a GIP fragment. The administering two vaccines to the same animal or human may additively, or preferably synergistically, increase the efficacy, as compared administering one vaccine only.

In one preferred embodiment, the at least one first composition and the at least one second composition are separately kept in the kit.

In another embodiment, the at least one first composition and the at least one second composition are mixed and kept as a mixture in the kit. Therefore, in a further aspect, the present invention provides for a composition comprising (a) at least one first virus-like particle (VLP) and at least one second virus-like particle (VLP) with each at least one first attachment site; and (b) at least one first antigen and at least one second antigen with each at least one second attachment site, wherein said at least one first antigen is GIP protein or a GIP fragment and said at least one second antigen comprises or is a molecule selected from the group consisting of: (i) a ghrelin or a ghrelin peptide, (ii) a nicotine, a cotinine or a nornicotine; and (iii) a second GIP protein or a second GIP fragment, wherein the second GIP protein or GIP fragment is different from the first GIP protein or GIP fragment, and wherein said at least one first virus-like particle (VLP) and said at least one first antigen are linked through said at least one first and said at least one second attachment site, and wherein said at least one second virus-like particle (VLP) and said at least one second antigen are linked through said at least one first and said at least one second attachment site. Thus the invention provides a vaccine composition comprises said composition. The vaccine composition may further comprise at least one adjuvant. Preferably the vaccine composition is devoid of an adjuvant. The invention further provides a method of immunization comprising administering said vaccine composition to an animal, preferably to a dog or to a cat, preferably to a domestic cat, or a human. Moreover, the invention provides a method of treating and/or preventing obesity comprising administering the vaccine composition to an animal, preferably to a domestic cat or a dog, or human. Furthermore, the invention provides a pharmaceutical composition comprising said composition and an acceptable pharmaceutical carrier.

It will be understood by one of ordinary skill in the relevant arts that other suitable modifications and adaptations to the methods and applications described herein are readily apparent and may be made without departing from the scope of the invention or any embodiment thereof. Having now described the present invention in detail, the same will be more clearly understood by reference to the following examples, which are included herewith for purposes of illustration only and are not intended to be limiting of the invention.

All documents cited herein are entirely incorporated herein by reference.

EXAMPLES

The terms "prior art VLPs" as well as the more specific terms "prior art Qβ VLPs", "prior art AP205 VLPs" and the like, as used within this example section, refer to VLPs obtained by recombinant expression from *E. coli* and subsequent purification as described in WO 02/056905, WO 04/007538.

Example 1

Chemically Synthesize GIP Fragments 1-15, 1-10, 4-13, 16-30, 28-42, 31-42 and GIP Protein 1-42

Mouse GIP fragments 1-15, 1-10, 4-13, 16-30 and 31-42 including a GC or CG linker sequence fused to either the N- or the C-terminus of the GIP fragments (SEQ ID NO:27, 29, 32, 43, 44) were chemically synthesized according to standard procedures.

GIP protein 1-42, including a GC linker sequence fused to the C-terminus, (SEQ ID NO: 30) and GIP fragment 28-42 including a CG linker fused to the N-terminus are chemically synthesized according to standard procedures.

In order to improve the solubility of N-terminal GIP fragments coupled to the prior art Qβ VLP, hydrophobic amino acid residues within the specific GIP fragment may be substituted. Polar, hydrophilic charged amino acids, such as lysine (lys) and aspartate (asp) are added or used to replace native GIP residues.

GIP fragment 1-14, including a DDC or GIP fragment 1-14 including a KKC linker sequence fused to the C-terminus of the GIP fragments are chemically synthesized according to standard procedures.

Example 2

Coupling of GIP 1-15-GC, GIP 1-10-GC, GIP 4-13-GC and CG-GIP-31-42 to the Prior Art Qβ, fr or HBcAg VLPs A solution of 2 ml of 2.0 mg/ml prior art Qβ VLP in 20 mM Hepes, 150 mM NaCl pH 7.2 was reacted for 30 minutes with 114.4 μl of a SMPH (Pierce) solution (from a 50 mM stock solution dissolved in DMSO) at 25° C. The reaction solution was subsequently dialyzed twice for 2 hours against 2 L of 20 mM Hepes, 150 mM NaCl, pH 7.2 at 4° C.

The dialysed, derivatized Qβ VLP was subsequently used to couple either the murine GIP 1-15-GC (SEQ ID No: 60), GIP 1-10-GC (SEQ ID NO:61), GIP 4-13-GC (SEQ ID No 62) or murine CG-GIP 31-42 peptide Briefly, 1 ml of derivatized Qβ VLP (at a concentration of 2 mg/ml) was reacted with 286 μl of a 10 mM peptide solution for 2 hours at 20° C. in 20 mM Hepes, 150 mM NaCl, pH 7.2. The coupling reactions were then centrifuged at 13 000 rpm for 5 minutes and the supernatants were collected and dialyzed once for 2 hours and then overnight against 2 L of 20 mM Hepes, 150 mM NaCl, pH 7.2 at 4° C.

The covalent chemical coupling of GIP peptides 1-15 and 31-42 to the Qβ VLP was assessed by SDS-PAGE using 12% Nu-PAGE gels (Invitrogen). Coomassie blue stained gels of the coupling reaction demonstrated the appearance of bands with molecular weights corresponding to those predicted for GIP peptides covalently linked to Qβ (FIG. 1). Coupling bands corresponding to one, two, three or four peptides coupled per subunit are indicated by arrows. The appearance of these additional bands as compared to derivatized Qβ VLP alone, demonstrates, that GIP CG-1-15 and GIP 31-42-GC were covalently coupled to Qβ VLP. The coupling efficiency [i.e. mol Qβ-GIP/mol Qβ monomer (total)] was estimated, by densitometric analysis of the Coomassie blue stained SDS-PAGE, to be between 1.8-2.3 GIP fragments per Qβ monomer. Similar coupling efficiencies were observed for GIP CG-1-10 and GIP 4-13-GC were covalently coupled to Qβ VLP (data not shown).

Coupling of GIP Fragments to fr VLPs 1 ml of derivatized fr VLP (at a concentration of 2 mg/ml) is reacted with 286 μl of a 10 mM GIP 1-15-GC, GIP 1-10-GC, GIP 4-13-GC or CG-GIP-31-42 for 2 hours at 20° C. in 20 mM Hepes, 150 mM NaCl, pH 7.2. The coupling reactions are then centrifuged at 13 000 rpm for 5 minutes and the supernatants are collected and dialyzed once for 2 hours and then overnight against 2 L of 20 mM Hepes, 150 mM NaCl, pH 7.2 at 4° C.

Coupling of GIP Fragments to HBcAg1-185-Lys

Construction of HBcAg1-185-Lys, its expression and purification have been substantially described in EXAMPLE 2-5 of WO 03/040164. 1 ml of derivatized HBcAg1-185-Lys VLP (at a concentration of 2 mg/ml) is reacted with 286 μl of a 10 mM GIP 1-15-GC, GIP 1-10-GC, GIP 4-13-GC or CG-GIP-31-42 for 2 hours at 20° C. in 20 mM Hepes, 150 mM NaCl, pH 7.2. The coupling reactions are then centrifuged at 13 000 rpm for 5 minutes and the supernatants are collected and dialyzed once for 2 hours and then overnight against 2 L of 20 mM Hepes, 150 mM NaCl, pH 7.2 at 4° C.

Example 3

Coupling of GIP 16-30-GC, CG-GIP 28-42, GIP 1-14-KKC, GIP 1-14-DDC and GIP 1-42-GC to Prior Art Qβ VLP A solution of 2 ml of 2.0 mg/ml Qβ VLP in 20 mM Hepes, 150 mM NaCl pH 7.2 is reacted for 30 minutes with 114.4 μl of a SMPH (Pierce) solution (from a 50 mM stock solution dissolved in DMSO) at 25° C. The reaction is then dialyzed twice for 2 hours against 2 L of 20 mM Hepes, 150 mM NaCl, pH 7.2 at 4° C.

The dialysed, derivatized Qβ VLP is subsequently used to couple murine GIP protein (SEQ ID NO: 30), murine CG-GIP 28-42, murine GIP 16-30-GC, GIP 1-14-KKC or GIP 1-14-DDC. Briefly, 1 ml of derivatized Qβ VLP (at a concentration of 2 mg/ml) is reacted with 286 μl of a 10 mM peptide solution for 2 hours at 20° C. in 20 mM Hepes, 150 mM NaCl, pH 7.2. The coupling reactions are then centrifuged at 13 000 rpm for 5 minutes and the supernatants are collected and dialyzed once for 2 hours and then overnight against 2 L of 20 mM Hepes, 150 mM NaCl, pH 7.2 at 4° C.

Coupled products are then analyzed by SDS-PAGE using 12% Nu-PAGE (Invitrogen) gels. Coupling products are then visualised by Coomassie Brilliant Blue staining of the gels.

Example 4

Immunization of Mice with GIP 1-15-GC, GIP 1-10-GC, GIP 4-13-GC or CG-GIP 31-42 Coupled to the Prior Art Qβ VLP Adult male, C57BL/6 mice (5 per group) were vaccinated with either murine GIP 1-15-GC, murine GIP 1-10-GC, murine GIP 4-13-GC or murine CG-GIP 31-42 coupled to the prior art Qβ VLP (obtained in EXAMPLE 2). 100 μg of dialyzed vaccine from each sample were diluted in PBS to a volume of 200 μl and injected subcutaneously (100 μl on two ventral sides) on days 0, 14, 28 and 42. The vaccine was administered without adjuvant. As a control, a group of mice was injected with PBS or VLP Qβ. Mice were bled retroorbitally on day 0, 15, 28, 43, 56 71, 91 and 105 and their sera analyzed by ELISA as described in EXAMPLE 5. TABLE 1 shows the average titers of GIP 1-15-specific, GIP 1-10-specific or GIP 31-42-specific antibodies. Results shown are the averages of 10 mice per group. ELISA titers are expressed as serum dilutions which lead to half maximal OD in the ELISA assay. In mice immunized with GIP 1-15-GC-Qβ, GIP 1-10-GC-Qβ or Qβ-CG-GIP 31-42, average titers of approximately 1:300 000, 1:330 000 and 1:82 000, respectively, were reached by day 56 (TABLE 1). GIP-specific titres from mice immunized with GIP 4-13-GC-Qβ were approximately 10-fold lower than GIP 1-15-specific titres (data not shown). Pre-immune sera or sera from mice injected with PBS or Qβ VLP did not show any reactivity against either GIP peptide. The half maximal OD titer was less than 100, which was considered to be below the cut-off of the assay. This clearly demonstrates that a GIP-VLP conjugate is able to induce a high antibody titer against GIP fragments, although it is a self protein. Antibody titers determined against GIP fragments coupled to RNAse were similar to the ones obtained against GIP protein (data not shown). This indicates that antibodies raised with GIP fragments were able to recognize GIP protein.

TABLE 1

Average anti-GIP specific IgG antibody titer (expressed as a dilution factor) in mice immunized on day 0, 14, 28 and 42 with GIP 1-15-GC-Qβ, GIP 1-10-GC-Qβ or Qβ-CG-GIP 31-42, respectively.

| Immunization | Days after first immunization | | | | |
|---|---|---|---|---|---|
| | 14 | 28 | 42 | 56 | 70 |
| Qb-GIP 1-15 | 75 463 | 263 598 | 266 839 | 306 169 | 239 527 |
| Qb-GIP 1-10 | 88 057 | 331 444 | 270 214 | 336 882 | 307 235 |
| Qb-GIP 31-42 | 15 480 | 47 974 | 70 815 | 82 066 | 70 458 |
| PBS or Qb VLP | 100 | 100 | 100 | 100 | 100 |

Example 5

Detection of GIP-Specific and Ghrelin-Specific Antibodies in an ELISA

First, murine GIP 1-15-GC or murine GC-GIP 31-42 was coupled to RNase (SIGMA)—SPDP (SIGMA) as described in the following paragraph. 5 mg/ml RNase and 0.2 mM SPDP (final concentration) was incubated for 1 h at RT. The RNase-SPDP solution was purified over a PD10 column (Amersham). After purification, 10 mM EDTA and 1 mM peptide was added to the RNase-SPDP solution. Coupling efficiency was determined by measuring OD at 343 nm.

ELISA plates (96 well MAXIsorp) were coated with RNase-coupled murine GIP 1-15-GC or murine CG-GIP 31-42 at a concentration of 10 μg/ml in coating buffer (0.1 M NaHCO3, pH 9.6), over night at 4° C. Alternatively, ELISA plates were coated with 2.5 μg/ml porcine GIP protein (Bachem). After washing the plates in wash buffer (PBS-0.05% Tween), the plates were blocked with blocking buffer (2% BSA-PBS-Tween 20 solution) for 2 h at 37° C. and then washed again and incubated with serially diluted mouse sera. As a control, pre-immune serum of the same mice was also tested. Plates were incubated at RT for 2 h. After further washing, bound antibodies were detected with a HRPO-labeled, Fc specific, goat anti-mouse IgG antibody (Jackson Immunoresearch) and incubated for 1 h at RT. After further washing, plates were developed with OPD solution (1 OPD tablet, 25 ul OPD buffer and 8 ul $H_2O_2$) for 6 minutes and the reaction was stopped with 5% $H_2SO_4$ solution. Plates were read at 450 nm on an ELISA reader (Biorad Benchmark). ELISA titers are expressed as serum dilutions which lead to half maximal OD in the ELISA assay.

In order to measure ghrelin-specific antibodies from the sera of mice immunised with Ghrelin24-31GC coupled to Qβ VLP, a method similar to the one described above was used. The only difference was that ELISA plates were coated with 20 ug/ml ghrelin protein (Bachem).

Example 6

Efficacy Experiments with GIP 1-15-GC-Qβ, GIP 1-10-GC-Qβ or Qβ-CG-GIP 31-42 Coupled to Prior Art Qβ VLP in a Diet Induced Animal Model of Obesity Adult male, C57BL/6 mice (5 per group) with comparable starting weights (22.7-23.1 g) were vaccinated, as described in EXAMPLE 4 with either murine GIP 1-15-GC, GIP 1-10-GC or murine CG-GIP 31-42 coupled to Qβ VLP, obtained in EXAMPLE 2. As a control, mice were injected with Qβ VLP. All mice were placed on a high fat diet (35% fat by weight, 60% as energy) after the first injection, in order to facilitate the development of diet-induced obesity. Food and water were administered ad libitum. The body weights of individual animals were monitored in regular intervals over a period of approximately 4 month after the first injection.

As shown in FIG. 2A, mice immunized with GIP-1-15-GC or CG-GIP 31-42 coupled to Qβ VLP gained less weight in the course of the experiment than the control animals, which had been injected Qβ VLP. In fact, 112 days after the first immunisation the control animals had increased their weight by roughly 110% whereas GIP 1-15-GC-Qβ and GC-GIP 31-42-Qβ VLP immunised mice had only increased their weight by 80% and 82%, respectively. Hence, both vaccinated groups displayed a clearly reduced weight gain compared to control groups. Results comparable to those achieved with GIP-1-15-GC-Qβ VLP were obtained with GIP-1-10-GC-Qβ (data not shown).

To further evaluate the effect of vaccination against GIP, changes in body fat mass were measured by dual energy X-ray absorptiometry scan (DEXA). DEXA analyses were performed by the ultra high resolution PIXIMUS Series Densitometer (0.18×0.18 mm pixels, GE Medical Systems). 142 days after the first injection DEXA analyses were performed. Mice immunized with GIP 1-15-GC or CG-GIP 31-42 coupled to Qβ VLP showed a reduction of body fat mass by approximately 26% and 22%, respectively (FIG. 2B), compared to Qβ VLP control animals. Similar results were obtained with GIP 1-10-GC coupled to Qβ VLP (data not shown). No differences in lean body mass were observed between vaccinated and control groups clearly indicating that the reduction in body weight was due to the reduction in body fat.

Taken together these results clearly demonstrate that a GIP-VLP conjugate is able to reduce body weight gain and body fat accumulation.

Example 7

Safety Experiments with GIP 1-15-GC-Qβ, GIP 1-10-GC-Qβ or Qβ-CG-GIP 31-42 Coupled to the Prior Art Qβ VLP in a Diet Induced Animal Model of Obesity To evaluate possible side-effects of vaccination against GIP, blood glucose, fructosamine and triglyceride levels were measured in vaccinated animals. Briefly, adult male C57BL/6 mice (five per group) were vaccinated as described in EXAMPLE 4 with GIP 1-15-GC or CG-GIP 31-42 coupled to Qβ VLP, obtained in EXAMPLE 2. As a control mice were injected with PBS or Qβ VLP.

Over 4 days, spaced two days apart between 91 and 102 days after the first immunisation, mice were bled twice in the morning (9.00 h) and twice in the evening (15.00 h) and blood glucose levels were determined using the Glucotrend blood glucose meter (Roche). During this period mice had free access to food and water. Averages of the respective evening and morning readings are shown in TABLE 4. No significant difference in blood glucose levels were observed between vaccinated and PBS injected animals. Similar results were observed in mice vaccinated with GIP 1-10-GC-Qβ (data not shown).

In the same animals the plasma triglyceride levels were determined 120 days after the first injection. Briefly, after a 12 h fasting period, blood samples were taken from the GIP 1-15-GC or CG-GIP 31-42 coupled to Qβ VLP immunised mice and from the PBS injected control mice. Triglyceride levels were then determined from plasma samples by enzymatic assays with an Olympus AU400 automated laboratory work station. The average values for each group and the standard deviations (n=5) are shown in TABLE 4. No significant differences were observed between the vaccinated and the control animals.

Furthermore, fructosamine levels were determined in the same animals at various time intervals after immunization. Fructosamine levels reflect the total amount of glycosylated protein in the circulation and if fructosamine levels are elevated they indicate increased glycemia. Since circulating fructosamine has a 3 week lifespan, fructosamine measurement provides a retrospective glycemic picture. Briefly, after a 12 h fasting period, blood samples were taken at various time intervals from the GIP 1-15-GC or CG-GIP 31-42 coupled to Qβ VLP immunised mice and from the PBS or Qβ VLP injected control mice. Fructosamine levels were then determined from plasma samples. The average values for each group and the standard deviations (n=5) are shown in TABLE 5. Overall, there were no significant differences observed between the vaccinated and the control animals. Despite, two significantly different time points per GIP 1-15-GC-Qβ or CG-GIP 31-42-Qβ vaccinated group (day 55 and 69, day 27 and 69, respectively), overall values fell within the normal fructosamine range of approximately 200-400 μmol/L. Fructosamine levels exceeding 400 μmol/L are considered a risk for the development of diabetes. Hence, vaccination against GIP does not induce a hyperglycaemic state in mice immunized with GIP 1-15-GC or CG-GIP 31-42 coupled to Qβ VLP.

In conclusion, no significant differences were observed in blood glucose levels, fasting triglyceride and fructosamine levels between the vaccinated (GIP 1-15-GC or CG-GIP 31-42 coupled to Qβ VLP) and control group (PBS or Qβ VLP injected animals), despite the presence of anti-GIP antibodies in the vaccinated mice (TABLE 2 and 3).

TABLE 2

Average morning and evening blood glucose levels and fasting triglyceride levels in 5 mice per group immunized with GIP 1-15-GC-Qβ or Qβ-CG-GIP 31-42.

| Immunization | Blood glucose ± SD (mg/dL) | | Triglycerides ± SD (mmol/L) | Anti-GIP peptide IgG titer |
|---|---|---|---|---|
| | 9.00 h | 15.00 h | after 12 h fast | Day 105 |
| Qb-GIP 1-15 | 132.1 ± 15.4 | 150.5 ± 21.8 | 0.48 ± 0.005 | 46 691 |
| Qb-GIP 31-42 | 125.4 ± 12.4 | 153.3 ± 26.8 | 0.63 ± 0.08 | 28 911 |
| PBS | 149.1 ± 23.4 | 160.0 ± 20.8 | 0.55 ± 0.02 | 100 |

TABLE 3

Average fasting fructosamine levels in 5 mice per group immunized with GIP
1-15-GC-Qβ or Qβ-CG-GIP 31-42.

| Immunization | Fructosamine level ± SEM (μmol/L) | | | | | | |
|---|---|---|---|---|---|---|---|
| | d 13 | d 27 | d 41 | d 55 | d 69 | d 84 | d 253 |
| Qb-GIP 1-15 | 238 ± 10 | 252 ± 13 | 237 ± 6 | 330 ± 18 | 352 ± 12 | 308 ± 30 | 206 ± 13 |
| Qb GIP 31-42 | 261 ± 15 | 296 ± 12 | 252 ± 17 | 311 ± 19 | 347 ± 35 | 280 ± 19 | 196 ± 12 |
| Qb | 251 ± 6 | 243 ± 13 | 248 ± 15 | 260 ± 6 | 289 ± 6 | 279 ± 7 | 207 ± 3 |
| PBS | 246 ± 5 | 230 ± 5 | 259 ± 4 | 256 ± 10 | 282 ± 7 | 262 ± 13 | 184 ± 9 |

Example 8

Immunization of Mice with GIP 16-30-GC, CG-GIP 28-42, GIP 1-14-KKC, GIP 1-14-DDC and GIP Protein 1-42-GC Coupled to the Prior Art Qβ VLP Adult, male or female, C57BL/6 mice are vaccinated with either murine GIP 16-30-GC, CG-GIP 28-42, GIP 1-14-KKC, GIP 1-14-DDC or GIP protein 1-42-GC coupled to Qβ VLP, obtained in EXAMPLE 3. Briefly, 100 μg of dialyzed vaccine from each sample is diluted in PBS to a volume of 200 μl and injected subcutaneously (100 μl on two ventral sides) on days 0, 14, 28 and 42 and subsequently as required. The vaccine is administered with or without adjuvant. As a control, a group of mice are immunized with Qβ VLP or injected with PBS, with or without adjuvant. Mice are bled retro-orbitally on day 0, 14, 28, 42 and subsequently at regular intervals. The GIP specific antibodies are then quantified by ELISA as described in EXAMPLE 5.

Example 9

Efficacy Experiments with GIP 4-13-GC, GIP 16-30-GC, CG-GIP 28-42, GIP 1-14-KKC, GIP 1-14-DDC and GIP Protein 1-42-GC Coupled to Qβ VLP in a Diet Induced Animal Model of Obesity Adult, male or female, C57BL/6 mice with comparable starting weights are vaccinated, as described in EXAMPLE 8 with either murine GIP 4-13-GC, GIP 16-30-GC, CG-GIP 28-42, GIP 1-14-KKC, GIP 1-14-DDC or GIP protein 1-42-GC coupled to Qβ VLP, obtained in EXAMPLE 3. As a control, mice are immunized with Qβ VLP alone or injected with PBS. Mice are subsequently boosted if GIP-specific antibody titers significantly decline during the experiment. All mice are placed on a high fat diet (35% fat by weight, 60% as energy) to facilitate the development of diet-induced obesity. Food and water is administered ad libitum. Body weights are monitored at regular intervals. In addition body fat mass, blood glucose levels and plasma triglyceride and fructosamine levels are determined at different intervals, as described in EXAMPLE 7.

Example 10

Efficacy Experiments with Murine GIP 1-15-GC, GIP 1-10-GC, GIP 4-13-GC, GIP 16-30-GC, CG-GIP 28-42, GIP 1-14-KKC, GIP 1-14-DDC and GIP protein 1-42-GC Coupled to Prior Art Qβ VLP in a Genetic Animal Model of Obesity Adult male or female, C57BL/6 ob/ob mice are vaccinated as described in EXAMPLE 8 with either murine GIP 1-15-GC, GIP 1-10-GC, GIP 4-13-GC, GIP 16-30-GC, CG-GIP 28-42, GIP 1-14-KKC, GIP 1-14-DDC or GIP protein 1-42-GC coupled to prior art Qβ VLP, obtained in EXAMPLE 2 or 3. As a control, mice are immunized with Qβ VLP or injected with PBS. Mice are subsequently boosted if GIP-specific antibody titers significantly decline over the period of the experiment. Mice are fed a standard diet (consisting of 4-10% fat by weight), ad libitum, and have free access to water. Body weights are monitored at regular intervals. In addition body fat mass, blood glucose levels and plasma triglyceride and fructosamine levels are determined at different intervals (as described in EXAMPLE 7).

Example 11

Efficacy Experiments with Murine GIP 1-15-GC, GIP 1-10-GC and CG-GIP 31-42 Coupled to Qβ VLP in a Therapeutic Diet-Induced Animal Model of Obesity Adult Male, C57BL/6 mice (10 per group) were fed a high fat diet, ad libitum, for approximately 14 weeks until they had become obese (weights >42 g). Then two experimental groups of similar average starting weights were made. The averages of the two groups differed by only <0.1 g at the start of the experiment.

After grouping, mice (10 per group) were vaccinated, as described in EXAMPLE 4, with murine GIP 1-15-GC, GIP 1-10-GC or CG-GIP 31-42 coupled to the prior art Qβ VLP, obtained in EXAMPLE 2. As a control mice were immunized with Qβ VLP. Mice were subsequently boosted if GIP-specific antibody titers significantly decline during the experiment.

Mice were bled retro-orbitally on day 0, 14, 28, 42, 56 and subsequently at monthly intervals, thereafter. The sera were analyzed for GIP-specific antibodies in a GIP-specific ELISA as described in EXAMPLE 5. GIP-specific antibodies titres induced by vaccination with GIP 1-15-GC, GIP 1-10-GC or CG-GIP 31-42 coupled to the prior art Qβ VLP were comparable to those shown in TABLE 1. Body weights were monitored at regular intervals. In addition body fat mass, blood glucose levels and plasma triglyceride levels are determined at different intervals, as described in EXAMPLE 7.

As shown in TABLE 4, mice immunized with GIP 1-15-GC, GIP 1-10-GC or CG-GIP 31-42 coupled to Qβ VLP gained less weight in the course of the experiment than the control animals, which had been injected Qβ VLP. By day 98 after the first immunisation the control animals had increased their weight by roughly 8.6 grams (20%) whereas GIP 1-15-GC-Qβ, GIP 1-10-GC-Qβ and GC-GIP 31-42-Qβ VLP immunised mice had decreased their weight by 0.5 g (3.0%), 0.6 g (−3.0%) and 0.2 g (−0.5%), respectively. Hence, all vaccinated groups clearly demonstrate a reduced weight gain compared to control groups, in a therapeutic setting.

TABLE 4

Average body weight change (expressed in percent) of 10 mice per group immunized with GIP 1-15-GC-Qβ, GIP 1-10-GC-Qβ or Qβ-CG-GIP 31-42 over 98 days.

| Immunization | Average body weight change ± SEM (%) | | | | | | |
|---|---|---|---|---|---|---|---|
| | d 14 | d 28 | d 42 | d 57 | d 70 | d 84 | d 98 |
| Qb-GIP 1-15 | 0.0 | −7.47 ± 1.9 | −5.90 ± 2.1 | −4.39 ± 1.7 | −2.69 ± 2.3 | 2.03 ± 2.2 | 3.11 ± 2.6 |
| Qb-GIP1-10 | 0.0 | −7.35 ± 2.1 | −4.19 ± 2.9 | −0.28 ± 3.5 | −0.02 ± 3.5 | 4.72 ± 3.9 | −0.39 ± 3.8 |
| Qb GIP 31-42 | 0.0 | −6.70 ± 0.7 | −5.98 ± 0.9 | −1.68 ± 1.3 | −1.71 ± 1.3 | 3.60 ± 1.4 | 2.27 ± 1.3 |
| Qb | 0.0 | −3.34 ± 0.2 | 1.86 ± 0.3 | 10.03 ± 0.4 | 12.22 ± 0.4 | 19.90 ± 0.4 | 19.64 ± 0.4 |

Example 12

Efficacy Experiments with Murine GIP 4-13-GC, GIP 16-30-GC, CG-GIP 28-42, GIP 1-14-KKC, GIP 1-14-DDC and GIP Protein 1-42-GC Coupled to Qβ VLP in a Therapeutic Diet-Induced Animal Model of Obesity Adult male or female, C57BL/6 mice are fed a high fat diet, ad libitum, for approximately 17-24 weeks or until they have become obese (weights >45 g). Mice are then grouped such that the distribution of the starting weights and the average starting weights are similar for all groups.

Mice are vaccinated as described in EXAMPLE 8, with either murine GIP 4-13-GC, GIP 16-30-GC, CG-GIP 28-42, GIP 1-14-KKC, GIP 1-14-DDC or GIP protein 1-42-GC coupled to Qβ VLP, obtained in example 3. As a control mice are immunized with Qβ VLP or injected with PBS. Mice are further boosted if GIP-specific antibody titers start to decline. Mice are bled retro-orbitally on day 0, 14, 28, 42, 56, 70 and then at monthly intervals. The sera are analyzed for GIP-specific antibodies by ELISA as described in EXAMPLE 5. Body weights are monitored at regular intervals. In addition body fat mass, blood glucose levels and plasma triglyceride and fructosamine levels are determined at different intervals, as described in EXAMPLE 7.

Example 13

Preparation of Qβ VLPs of the Invention by Disassembly/Reassembly in the Presence of Different Polyanionic Macromolecules Resulting in Reassembled Qβ VLPs (A) Disassembly of Prior Art Qβ VLP 45 mg prior art Qβ VLP (2.5 mg/ml, as determined by Bradford analysis) in PBS (20 mM Phosphate, 150 mM NaCl, pH 7.5) purified from E. coli lysate was reduced with 10 mM DTT for 15 min at room temperature under stirring conditions. Magnesium chloride was then added to 0.7 M final concentration and the incubation was continued for 15 min at room temperature under stirring conditions, which led to the precipitation of the encapsulated host cell RNA. The solution was centrifuged for 10 min at 4000 rpm at 4° C. (Eppendorf 5810 R, in fixed angle rotor A-4-62 used in all following steps) in order to remove the precipitated RNA from the solution. The supernatant, containing the released, dimeric Qβ coat protein, was used for the chromatographic purification steps.

(B) Purification of the Qβ Coat Protein by Cation Exchange Chromatography and by Size Exclusion Chromatography The supernatant of the disassembly reaction, containing the dimeric coat protein, host cell proteins and residual host cell RNA, was diluted 1:15 in water to adjust conductivity below 10 mS/cm and was loaded onto a SP-Sepharose FF column (xk16/20, 6 ml, Amersham Bioscience). The column was equilibrated beforehand with 20 mM sodium phosphate buffer pH 7. The elution of the bound coat protein was accomplished by a step gradient to 20 mM sodium phosphate/500 mM sodium chloride and the protein was collected in a fraction volume of approx. 25 ml. The chromatography was carried out at room temperature with a flow rate of 5 ml/min and the absorbance was monitored at 260 nm and 280° nm.

In the second step, the isolated Qβ coat protein (the eluted fraction from the cation exchange column) was loaded (in two runs) onto a Sephacryl S-100 HR column (xk26/60, 320 ml, Amersham Bioscience), equilibrated with 20 mM sodium phosphate/250 mM sodium chloride; pH 6.5. The chromatography was carried out at room temperature with a flow rate of 2.5 ml/min and the absorbance was monitored at 260 nm and 280 nm. Fractions of 5 ml were collected.

(C1) Reassembly of the Qβ VLP by Dialysis

Purified Qβ coat protein (2.2 mg/ml in 20 mM sodium phosphate pH 6.5), one polyanionic macromolecule (2 mg/ml in water), urea (7.2 M in water) and DTT (0.5 M in water) were mixed to the final concentrations of 1.4 mg/ml coat protein, 0.14 mg/ml of the respective polyanionic macromolecule, 1 M urea and 2.5 mM DTT. The mixtures (1 ml each) were dialyzed for 2 days at 5° C. in 20 mM TrisHCl, 150 mM NaCl pH 8, using membranes with 3.5 kDa cut off. The polyanionic macromolecules were: polygalacturonic acid (25000-50000, Fluka), dextran sulfate (MW 5000 and 10000, Sigma), poly-L-aspartic acid (MW 11000 and 33400, Sigma), poly-L-glutamic acid (MW 3000, 13600 and 84600, Sigma) and tRNAs from bakers yeast and wheat germ.

(C2) Reassembly of the Qβ VLP by Diafiltration 33 ml purified Qβ coat protein (1.5 mg/ml in 20 mM sodium phosphate pH 6.5, 250 mM NaCl) was mixed with water and urea (7.2 M in water), NaCl (5 M in water) and poly-L-glutamic acid (2 mg/ml in water, MW: 84600). The volume of the mixture was 50 ml and the final concentrations of the components were 1 mg/ml coat protein, 300 mM NaCl, 1.0 M urea and 0.2 mg/ml poly-L-glutamic acid. The mixture was then diafiltrated at room temperature, against 500 ml of 20 mM TrisHCl pH 8, 50 mM NaCl, applying a cross flow rate of 10 ml/min and a permeate flow rate of 2.5 ml/min, in a tangential flow filtration apparatus using a Pellicon XL membrane cartridge (Biomax 5K, Millipore).

Example 14

In Vitro Assembly of AP205 VLPs (A) Purification of AP205 Coat Protein

Disassembly: 20 ml of AP205 VLP solution (in 1.6 mg/ml PBS, purified from E. coli extract) was mixed with 0.2 ml of 0.5 M DTT and incubated for 30 min at room temperature. 5 ml of 5 M NaCl was added and the mixture was then incubated for 15 min at 60° C., causing precipitation of the DTT-reduced coat proteins. The turbid mixture was centrifuged (rotor Sorvall SS34, 10000 g, 10 min, 20° C.) and the supernatant was discarded and the pellet was dispersed in 20 ml of 1 M Urea/20 mM Na Citrate pH 3.2. After stirring for 30 min at room temperature, the dispersion was adjusted to pH 6.5 by addition of 1.5 M Na$_2$HPO$_4$ and then centrifuged (rotor Sorvall SS34, 10000 g, 10 min, 20° C.) to obtain supernatant containing dimeric coat protein.

Cation exchange chromatography: The supernatant (see above) was diluted with 20 ml water to adjust a conductivity of approx. 5 mS/cm. The resulting solution was loaded on a column of 6 ml SP Sepharose FF (Amersham Bioscience) which was previously equilibrated with 20 mM sodium phosphate pH 6.5 buffer. After loading, the column was washed with 48 ml of 20 mM sodium phosphate pH 6.5 buffer followed by elution of the bound coat protein by a linear gradient to 1 M NaCl over 20 column volumes. The fractions of the main peak were pooled and analyzed by SDS-PAGE and UV spectroscopy. According to SDS-PAGE, the isolated coat protein was essentially pure from other protein contaminations. According to the UV spectroscopy, the protein concentration was 0.6 mg/ml (total amount 12 mg), taking that 1 A280 unit reflects 1.01 mg/ml of AP205 coat protein. Furthermore, the value of A280 (0.5999) over the value of A260 (0.291) is 2, indicating that the preparation is essentially free of nucleic acids.

(B) Assembly of AP205 VLPs

Assembly in the absence of any polyanionic macromolecule: The eluted protein fraction from above was diafiltrated and concentrated by TFF to a protein concentration of 1 mg/ml in 20 mM sodium phosphate pH 6.5. 500 µl of that solution was mixed with 50 µl of 5 M NaCl solution and incubated for 48 h at room temperature. The formation of reassembled VLPs in the mixture was shown by non-reducing SDS-PAGE and by size exclusion HPLC. A TSKgel G5000 PWXL column (Tosoh Bioscience), equilibrated with 20 mM sodium phosphate, 150 mM NaCl pH 7.2, was used for the HPLC analysis.

Assembly in the presence of polyglutamic acid: 375 µl of purified AP205 coat protein (1 mg/ml in 20 mM sodium phosphate pH 6.5) was mixed with 50 µl of NaCl stock solution (5 M in water) solution, 50 µl of polyglutamic acid stock solution (2 mg/ml in water, MW: 86400, Sigma) and 25 µl of water. The mixture was incubated for 48 h at room temperature. The formation of reassembled VLP in the mixture was shown by non-reducing SDS-PAGE and by size exclusion HPLC. The coat protein in the mixture was almost completely incorporated into the VLPs, showing higher assembly efficiency than the AP205 coat protein assembled in the absence of any polyanionic macromolecule.

Example 15

Coupling GIP Fragments 1-10, 4-13, 1-15, 31-42, 16-30, 28-42, 1-14-KKC, GIP 1-14-DDC and GIP Protein 1-42 to the Reassembled Qβ or to the Reassembled AP205 VLP A solution of 2 ml of 2.0 mg/ml reassembled Qβ VLP (obtained in EXAMPLE 13) in 20 mM Hepes, 150 mM NaCl pH 7.2 is reacted for 30 minutes with 114.4 µl of a SMPH (Pierce) solution (from a 50 mM stock solution dissolved in DMSO) at 25° C. The reaction solution is subsequently dialyzed twice for 2 hours against 2 L of 20 mM Hepes, 150 mM NaCl, pH 7.2 at 4° C.

The dialysed, derivatized reassembled Qβ VLP is subsequently used to couple the murine GIP 1-15-GC, murine CG-GIP 31-42 peptide, murine GIP 1-10-GC, murine GIP 4-13 GC, murine GIP 16-30-GC, murine CG-GIP 28-42, murine GIP 1-14-KKC, murine GIP 1-14-DDC or murine GIP protein 1-42-GC. Briefly, 1 ml of derivatized reassembled Qβ VLP (at a concentration of 2 mg/ml) is reacted with 286 µl of a 10 mM peptide solution for 2 hours at 20° C. in 20 mM Hepes, 150 mM NaCl, pH 7.2. Then the coupling reactions are centrifuged at 13 000 rpm for 5 minutes and the supernatants are collected and dialyzed once for 2 hours and then overnight against 2 L of 20 mM Hepes, 150 mM NaCl, pH 7.2 at 4° C.

The solution of 2 ml of 2.0 mg/ml reassembled AP205 VLP (obtained in EXAMPLE 14) in 20 mM Hepes, 150 mM NaCl pH 7.2 is first derivatized by SMPH under identical or similar conditions as described reassembled Qβ VLP. The derivatized reassembled AP205 VLP is then reacted with the GIP fragments as described in the last paragraph under similar or identical conditions.

Example 16

Immunization and Efficacy Experiments with Murine GIP 1-10-GC, GIP 1-15-GC; GIP 4-13-GC, GIP 16-30-GC, CG-GIP 28-42, GIP 1-14-KKC, GIP 1-14-DDC CG-GIP 31-42 and GIP Protein 1-42-GC Coupled to the Reassembled Qβ VLP or to the Reassembled AP205 VLP in a Therapeutic Diet-Induced Animal Model of Obesity Adult male or female, C57BL/6 mice are fed a high fat diet, ad libitum, for approximately 17-24 weeks or until the mice have become obese (weights >45 g). Mice are then grouped such that the distribution of the starting weights and the average starting weights are similar for all groups.

Mice are vaccinated as described in EXAMPLE 8 with either murine GIP 1-10-GC, GIP 4-13-GC, GIP 1-15-GC, GIP 16-30-GC, CG-GIP 28-42, GIP 1-14-KKC, GIP 1-14-DDC, CG-GIP 31-42 or GIP protein 1-42-GC coupled to the reassembled Qβ VLP obtained in EXAMPLE 15. Control mice are immunized with the reassembled Qβ VLP (obtained in EXAMPLE 13) or injected with PBS. 100 µg of dialyzed vaccine or control protein is diluted in a 200 µl volume of PBS and injected subcutaneously (100 µl on two ventral sides), with or without adjuvant, on day 0. Mice are boosted with the corresponding formulation on day 14, 28 and 42. Mice are further boosted if GIP-specific antibody titers start to decline.

Mice are bled retro-orbitally on day 0, 14, 28, 42, 56, 70 and then subsequently at regular intervals. The sera are analyzed for GIP-specific antibodies by ELISA, as described in EXAMPLE 5. Body weights are monitored at regular intervals. In addition body fat mass, blood glucose levels and plasma triglyceride and fructosamine levels are determined at different intervals as described in EXAMPLE 7.

Similar, analogous or identical conditions are applied to test the efficacy of the reassembled AP205 VLP coupled to GIP fragments or GIP protein in the mouse therapeutic diet-induced model of obesity.

Example 17

Coupling Ghrelin 24-31GC to the Prior Art Qβ VLP

The ghrelin-peptide Ghrel24-31GC (GSSFLSPEGC SEQ ID NO:39), which comprises an added C-terminal cysteine residue for coupling to VLPs, was chemically synthesized, and used for chemical coupling to Qβ as described below.

A solution of 5 ml of 140 μM prior art Qβ VLPs in 20 mM Hepes, 150 mM NaCl pH 7.4 was reacted for 30 minutes with 108 μl of a 65 mM solution of SMPH (Pierce) in $H_2O$ at 25° C. on a rocking shaker. The reaction solution was subsequently dialyzed twice for 2 hours against 5 L of 20 mM Hepes, 150 mM NaCl, pH 7.2 at 4° C. 100 μl of the dialyzed reaction mixture was then reacted either with 28.6 μl of a 10 mM stock solution (in DMSO) of the ghrelin-peptide (1:10 peptide/Qβ capsid protein ratio). The coupling reaction was performed for 2 h at 15° C. in a water bath. The reaction mixture was then centrifuged at 13 000 rpm for 5 minutes and the supernatants were collected and dialyzed once for 2 hours and then overnight against 2×5 L of 20 mM Hepes, 150 mM NaCl, pH 7.2 at 4° C.

The coupling reaction was analysed on 16% SDS-PAGE gels under reducing conditions. Gels were stained with Coomassie Brilliant Blue.

Example 18

Co-Immunization of Mice with GIP 1-15-GC Coupled to Qβ VLP and Ghre124-31-GC Coupled to Qβ VLP Adult, male or female, C57BL/6 mice are vaccinated simultaneously with murine GIP 1-15-GC coupled to Qβ VLP (obtained from EXAMPLE 2) and murine ghre124-31-GC coupled to Qβ VLP (obtained from EXAMPLE 17). 100 μg of each dialyzed vaccine are combined and diluted in PBS to a volume of 200 μl and injected subcutaneously (100 μl on two ventral sides) on days 0, 14, 28 and 42 and subsequently as required. The two-vaccine combination is administered with or without adjuvant. As a control, a group of mice is immunized with Qβ VLP alone or injected with PBS, with or without adjuvant. Mice are bled retro-orbitally on day 0, 14, 28, 42 and subsequently at regular intervals. Their serum is analyzed for anti-GIP and anti-ghrelin antibodies by ELISA, as described in EXAMPLE 5.

Similar, analogous or identical experimental conditions are applied to immunize

Adult, male or female, C57BL/6 mice simultaneously with murine GIP 1-15-GC coupled to reassembled Qβ VLP and murine ghre124-31-GC coupled to reassembled Qβ VLP. Mice are bled retro-orbitally on day 0, 14, 28, 42 and subsequently at regular intervals and their serum is analyzed for anti-GIP and anti-ghrelin antibodies using a GIP-specific or Ghrelin-specific ELISA, respectively, as described in EXAMPLE 5.

Example 19

Efficacy Experiments with Co-Immunization of GIP 1-15-GC Coupled to Qβ VLP and Ghre124-31-GC Coupled to Qβ VLP in a Diet Induced Model of Obesity Adult, male or female, C57BL/6 mice with comparable starting weights are vaccinated with both murine GIP 1-15-GC coupled to the prior art Qβ VLP or the reassembled murine ghre124-31-GC coupled to the prior art Qβ VLP, as described in EXAMPLE 18. As a control, mice are immunized with the prior art Qβ VLP or the reassembled Qβ VLP alone or injected with PBS. Mice are subsequently boosted if GIP-specific or Ghrelin-specific antibody titers significantly decline during the experiment. All mice are placed on a high fat diet (35% fat by weight, 60% as energy) to facilitate the development of diet-induced obesity. Mice are bled retro-orbitally on day 0, 14, 28, 42 and subsequently at regular intervals. Their serum is analyzed for anti-GIP and anti-ghrelin antibodies by ELISA, as described in EXAMPLE 5.

Food and water is administered ad libitum. Body weights are monitored at regular intervals. In addition body fat mass, blood glucose levels and plasma triglyceride levels are determined at different intervals as described in EXAMPLE 7.

Example 20

Efficacy Experiments with Co-Immunization of GIP 1-15-GC Coupled to Qβ VLP and Ghrelin 24-31-GC Coupled to Qβ VLP in a Genetic Animal Model of Obesity Adult male or female, C57BL/6 ob/ob mice are vaccinated simultaneously with murine GIP 1-15-GC coupled to the prior art Qβ VLP or the reassembled Qβ VLP and murine ghrelin 24-31-GC coupled to the prior art Qβ VLP or the reassembled Qβ VLP, as described in EXAMPLE 18. As a control, mice are immunized with the prior art Qβ VLP alone, the reassembled Qβ VLP or injected with PBS. Mice are subsequently boosted if GIP-specific or Ghrelin-specific antibody titers significantly decline over the period of the experiment. Mice are fed a standard diet.

Mice are bled retro-orbitally on day 0, 14, 28, 42 and subsequently at regular intervals. The sera are analyzed for anti-GIP and anti-ghrelin by ELISA as described in EXAMPLE 5. Body weights are monitored at regular intervals. In addition body fat mass, blood glucose levels and plasma triglyceride levels are determined at different intervals as described in EXAMPLE 7.

Example 21

Efficacy Experiments with Co-Immunization of GIP 1-15-GC Coupled to Qβ VLP and Ghrelin 24-31-GC Coupled to Qβ VLP in a Therapeutic Diet-Induced Animal Model of Obesity Adult male or female, C57BL/6 mice are fed a high fat diet, ad libitum, for approximately 17-24 weeks or until they have become obese (weight >45 g). Mice are then grouped such that the distribution of the starting weights and the average starting weights are similar for all groups Mice are vaccinated simultaneously with both, murine GIP 1-15-GC coupled to the prior art Qβ VLP or the reassemble Qβ VLP and murine ghrelin 24-31-GC coupled to the prior art Qβ VLP or the reassembled Qβ VLP, as described in EXAMPLE 18. Control mice are immunized with the prior art Qβ VLP or the reassembled Qβ VLP or injected with PBS. Mice are subsequently boosted if GIP-specific or Ghrelin-specific antibody titers significantly decline during the experiment.

Mice are bled retro-orbitally on day 0, 14, 28, 42 and subsequently at regular intervals. The sera are analyzed for anti-GIP and anti-ghrelin antibodies by ELISA as described in EXAMPLE 5. Body weights and body fat composition are monitored in individual mice after immunisation. In addition blood glucose and triglyceride levels are monitored at different intervals as described in EXAMPLE 7.

Example 22

Co-Immunization of Mice with GIP 1-15-GC Coupled to Qβ VLP and CG-GIP 31-42 Coupled to Qβ VLP Adult, male or female, C57BL/6 mice were vaccinated simultaneously with murine GIP 1-15-GC coupled to Qβ VLP and murine CG-GIP 31-42 coupled to Qβ VLP (both obtained from EXAMPLE 2). 100 μg of each dialyzed vaccine was combined and diluted in PBS to a volume of 200 μl and injected subcutaneously (100 μl on two ventral sides) on days 0, 14, 28 and 42 and subsequently as required. The two-vaccine combination was administered without adjuvant. As control, mice were immunized with Qβ VLP alone or injected with PBS. Mice are bled retro-orbitally on day 0, 14, 28, 42 and subsequently at regular intervals. Their serum was analyzed for anti-GIP specific antibodies by ELISA by coating full length mouse GIP protein to the plates, as described in EXAMPLE 5. GIP-specific antibody titres were comparable to those shown in TABLE 1.

Example 23

Efficacy Experiments with Co-Immunization of GIP 1-15-GC Coupled to Qβ VLP and CG-GIP 31-42 Coupled to Qβ VLP in a Diet Induced Model of Obesity Adult, male or female, C57BL/6 mice with comparable starting weights were vaccinated with both murine GIP 1-15-GC coupled to Qβ VLP and CG-GIP 31-42 coupled to Qβ VLP, as described in EXAMPLE 22. As a control, mice were immunized with the prior art Qβ VLP or injected with PBS. Mice were subsequently boosted if GIP-specific antibody titers significantly decline during the experiment. All mice were placed on a high fat diet (35% fat by weight, 60% as energy) to facilitate the development of diet-induced obesity. Mice were bled retro-orbitally on day 0, 14, 28, 42 and subsequently at regular intervals. Their serum was analyzed for anti-GIP antibodies by ELISA, as described in EXAMPLE 5. GIP-specific antibody titres were comparable to those shown in TABLE 1.

Food and water was administered ad libitum. Body weights were monitored at regular intervals. In addition body fat mass, blood glucose levels and plasma triglyceride and fructosamine levels are determined at different intervals as described in EXAMPLE 7. Average body weight gain in co-immunized mice was comparable to that observed with single immunization, as shown in TABLE 2.

Example 24

Immunization of Mice with AP205 Fused C-Terminally to the GIP 1-15 Peptide

The DNA fragment coding for the GIP peptide (YAEGTFISDYSIAMD, SEQ ID NO: 27), was created in three consecutive PCR reactions. In the first reaction, plasmid pAP405 was used as template, to amplify the gene of AP205 coat protein with oligo p1.45 (5'-AA TCTAGAATTTTCTGCGCACCCATCCCGG-3', SEQ ID NO 73) containing a Xba I site, and oligo p4.175 (5'-AAT-GAACGTGCCCTCTGCGTATCCGGAACCGCCTC CTGC-3', SEQ ID NO: 74), to add a nucleotide sequence coding the amino acid sequence YAEGTFI at the 3' of the nucleotide sequence encoding GTAGGGSG in the 3' region of AP205 coat protein gene in plasmid pAP405. Next, oligos p1.45 and p4.176 (5'-CATCGC GATCGAGTAATCG-GAAATGAACGTGCCCTCTGCGTA-3', SEQ ID NO:75) were used to amplify the PCR product of the first reaction, thereby adding a nucleotide sequence encoding the amino acid sequence SDYSIAM at the 3' end of the product of the first reaction. In the third reaction, oligos p1.45 and p4.177 (5'-ACATGCATTAATCCATCGC GATCGAGTAATC-3', SEQ ID NO: 76) were used to amplify the product of the second reaction thereby adding to the 3' end of the second PCR product a nucleotide sequence coding for the remaining Asp, containing a stop codon and the Mph1103I restriction site. The obtained fragment was digested with XbaI and Mph1103I and cloned in the same restriction sites into the vector pAP283 (AP205 patent), under the control of *E. coli* tryptophan operon promoter. The resulting construct was:

515 AP205 coat protein—GTAGGGSG-YAEGTFISDYS-IAMD

The method of purification of the expressed fusion protein is substantially the same as disclosed in EXAMPLE 2 of PCT/EP2005/054721. The construction and sequence of PAP405 and pAP283 are described in PCT/EP2005/054721 and in WO2004/007538A2, receptively.

Adult female, C57BL/6 mice (5 per group) were vaccinated with AP205 fused C-terminally to the GIP 1-15 peptide. 50 μg of dialyzed vaccine was diluted in PBS to a volume of 200 μl and injected subcutaneously (100 μl on two ventral sides) on days 0, 14, 28 and 42. The vaccine was administered without adjuvant. As a control, a group of mice was injected with PBS or AP205 VLP alone. Mice were bled retro-orbitally on day 0, 14, 28, 42, 56 and 70 and their sera analyzed by ELISA as described in EXAMPLE 5. TABLE 5 shows the average titers of GIP-specific antibodies. Results shown are the averages of 5 mice per group. ELISA titers are expressed as serum dilutions which lead to half maximal OD in the ELISA assay. In mice immunized with AP205 fused C-terminally to the GIP 1-15 peptide, average titers of approximately 1:184 000 were reached by day 42 (TABLE 7). Pre-immune sera or sera from mice injected with PBS or Qβ VLP did not show any reactivity against either GIP peptide. The half maximal OD titer was less than 100, which was considered to be below the cut-off of the assay. This clearly demonstrates that a GIP-VLP fusion is able to induce a high antibody titer against GIP fragments, although it is a self protein.

TABLE 5

Average anti-GIP specific IgG antibody titer (expressed as a dilution factor) in mice immunized on day 0, 14, 28 and 42 with AP205 fused C-terminally to the GIP 1-15 peptide.

| | Days after first immunization | | | | |
|---|---|---|---|---|---|
| Immunization | 14 | 28 | 42 | 56 | 70 |
| AP205-f-GIP | 7 000 ± 900 | 51 000 ± 16 800 | 184 477 ± 59 000 | 156 107 ± 43 000 | 106 100 ± 22 600 |
| PBS or AP205 | 100 | 100 | 100 | 100 | 100 |

Example 25

Effect on Glucose Tolerance with GIP 1-15-GC-Qβ Coupled to the Prior Art Qβ VLP in a Diet Induced Animal Model of Obesity To evaluate the possible effects on glucose tolerance an oral glucose tolerance test (OGTT) was performed in vaccinated animals. Briefly, adult female C57BL/6 mice (five per group) were vaccinated as described in EXAMPLE 4 with GIP 1-15-GC coupled to Qβ VLP, obtained in EXAMPLE 2. As a control mice were injected with Qβ VLP. A further boost was administered on day 122, twenty days prior to the OGTT. All mice were kept on a high fat diet for the duration of the experimental period.

On day 142 and after a 16 h fasting period, mice were administered a 2 g/kg D-glucose solution by oral gavage. Mice were bled via the tail vein at 0, 15, 30, 45, 60, 120 and 180 minutes after oral glucose administration. Blood glucose levels were determined using the Accu-check blood glucose meter (Roche). During this period mice continued to be fasted. The kinetics of the blood glucose response is shown in TABLE 6. No significant difference in the kinetics of the glucose response was observed between vaccinated and control animals.

Hence, vaccination against GIP does not induce impaired glucose tolerance in mice immunized with GIP 1-15-GC coupled to Qβ VLP.

Example 26

Effect on Insulin Responsiveness with GIP 1-15-GC-Qβ Coupled to the Prior Art Qβ VLP in a Diet Induced Animal Model of Obesity To evaluate the possible effects on insulin responsiveness an insulin sensitivity test (IST) was performed in vaccinated animals. Briefly, adult female C57BL/6 mice (4-5 per group) were vaccinated as described in EXAMPLE 4 with GIP 1-15-GC coupled to Qβ VLP, obtained in EXAMPLE 2. As a control mice were injected with Qβ VLP. A further boost was administered on day 122, twenty one days prior to the IST. All mice were kept on a high fat diet for the duration of the experimental period.

On day 143 and after a 16 h fasting period, mice were administered 0.5 U/kg of porcine insulin, intraperitoneally (IP). Mice were bled via the tail vein at 0, 15, 30, 45, 60 and 90 minutes after insulin administration. Blood glucose levels were determined using the Accu-check blood glucose meter (Roche). During this period mice continued to be fasted. The kinetics of the blood glucose response after IPIST is shown in TABLE 9. GIP 1-15-GC-Qβ vaccinated mice showed improved insulin sensitivity compared to Qβ VLP vaccinated control animals. The differences were significant at 0, 30, 45 and 60 minute after insulin administration.

Hence, vaccination against GIP improves insulin responsiveness in mice immunized with GIP 1-15-GC coupled to Qβ VLP.

TABLE 6

Blood glucose levels in an OGTT in 5 mice per group immunized with GIP 1-15-GC-Qβ.

| | Blood glucose levels after OGTT ± SEM | | | | | | |
|---|---|---|---|---|---|---|---|
| Immunization | 0' | 15' | 30' | 45' | 60' | 120' | 180' |
| Qb-GIP 1-15 | 110 ± 4.2 | 322 ± 18.8 | 290 ± 27.4 | 206 ± 10.7 | 181 ± 1.9 | 113 ± 3.8 | 97 ± 3.2 |
| Qb VLP | 118 ± 8.2 | 321 ± 9.9 | 245 ± 17.8 | 212 ± 5.6 | 194 ± 7.7 | 127 ± 3.1 | 120 ± 7.1 |

TABLE 7

Blood glucose levels in an IPIST in 4-5 mice per group immunized with GIP 1-15-GC-Qβ.

| Immunization | Blood glucose levels after IPIST ± SEM | | | | | |
| --- | --- | --- | --- | --- | --- | --- |
| | 0' | 15' | 30' | 45' | 60' | 90' |
| Qb-GIP 1-15 | 94 ± 5.2 | 76 ± 5.6 | 54 ± 3.7 | 42 ± 1.8 | 40 ± 2.9 | 45 ± 2.6 |
| Qb VLP | 116 ± 6.3 | 77 ± 3.8 | 66 ± 2.3 | 60 ± 5.1 | 52 ± 2.3 | 55 ± 5.6 |

---

What is claimed is:

1. A composition comprising:
   (a) a virus-like particle (VLP) of an RNA-bacteriophage with at least one first attachment site; and
   (b) at least one antigen with at least one second attachment site,
      wherein said at least one antigen is selected for its ability to induce an immune response against GIP when linked to said VLP, and wherein said at least one antigen is a GIP protein or a GIP fragment and wherein (a) and (b) are linked through said at least one first and said at least one second attachment site.

2. The composition of claim 1, wherein said GIP protein comprises an amino acid sequence selected from the group consisting of:
   (a) SEQ ID NO:22;
   (b) SEQ ID NO:23;
   (c) SEQ ID NO:24;
   (d) SEQ ID NO:25;
   (e) SEQ ID NO:26;
   (f) SEQ ID NO:63;
   (g) the GIP corresponding orthologs from any other animals; and
   (h) an amino acid sequence which is at least 80% identical with any one of (a) to (f).

3. The composition of claim 1, wherein said GIP fragment comprises an amino acid sequence selected from the group consisting of:
   (a) SEQ ID NO: 27;
   (b) SEQ ID NO: 29;
   (c) SEQ ID NO:32;
   (d) SEQ ID NO:45; and
   (e) an amino acid sequence which is at least 80% identical with SEQ ID NO: 27, 29, 32, or 45.

4. The composition of claim 1, wherein said RNA-phage is RNA-phage Qβ, fr, GA or AP205.

5. The composition of claim 1, wherein said first attachment site is linked to said second attachment site via at least one covalent non-peptide bond.

6. The composition of claim 1, wherein said first attachment site comprises an amino group of a lysine and wherein said second attachment site comprises a sulfhydryl group of a cysteine.

7. The composition of claim 1, wherein said GIP protein or GIP fragment is fused to the N- or C-terminus of the coat protein, mutants or fragments thereof, of RNA phage AP205.

8. The composition of claim 1 further comprising a linker, wherein said linker comprises said second attachment site, and wherein said linker is associated to said GIP protein or said GIP fragment by way of one peptide bond, and wherein said linker comprises a cysteine residue.

9. A method of immunization comprising administering said composition of claim 1 to a dog, a cat, or a human.

10. A pharmaceutical composition comprising:
    (a) the composition of claim 1, and
    (b) an acceptable pharmaceutical carrier.

11. A method of producing the composition claim 1 comprising:
    (a) providing a VLP of an RNA-bacteriophage with at least one first attachment site;
    (b) providing at least one antigen selected for its ability to induce an immune response against GIP when linked to said VLP, and wherein said at least one antigen is a GIP protein or a GIP fragment, with at least one second attachment site; and (c) linking said VLP of an RNA-bacteriophage to said at least one antigen through said at least one first attachment site and said at least one second attachment site to produce said composition.

12. A method of treating and/or preventing obesity comprising administering the composition of claim 1 to a domestic cat, a dog, or a human.

13. The composition of claim 1, wherein said at least one antigen is a GIP fragment.

14. The composition of claim 13, wherein said GIP fragment comprises the amino acid sequence set forth in SEQ ID NO:27.

15. The composition of claim 14, wherein said GIP fragment further comprises a stretch of hydrophilic amino acids fused to said GIP fragment.

16. The composition of claim 15, wherein said stretch of hydrophilic amino acids consists of one amino acid.

17. The composition of claim 16, wherein said one amino acid is lysine.

18. The composition of claim 1, wherein said at least one first attachment site and said at least one second attachment site are linked through one heterobifunctional cross-linker.

19. The composition of claim 8, wherein said linker is added to the C terminus of said GIP fragment.

20. The composition of claim 1, wherein said virus-like particle of an RNA-bacteriophage comprises recombinant coat proteins having the amino acid sequence as set forth in SEQ ID NO:1.

* * * * *

SEQUENCE LISTING

<160> NUMBER OF SEQ ID NOS: 76

<210> SEQ ID NO 1
<211> LENGTH: 132
<212> TYPE: PRT
<213> ORGANISM: Bacteriophage Q-beta

<400> SEQUENCE: 1

```
Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130
```

<210> SEQ ID NO 2
<211> LENGTH: 329
<212> TYPE: PRT
<213> ORGANISM: Bacteriophage Q-beta

<400> SEQUENCE: 2

```
Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95
```

```
Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr Trp Thr Leu Leu Ile Ala Gly Gly Ser Gly
    130                 135                 140

Ser Lys Pro Asp Pro Val Ile Pro Asp Pro Ile Asp Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
        195                 200                 205

Gly Asn Thr Lys Trp Arg Asp Trp Asp Ser Arg Leu Ser Tyr Thr Thr
    210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
        275                 280                 285

Ala Asp Gly Val Ile Val Gly Phe Trp Arg Asp Pro Ser Ser Gly Gly
    290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
                325

<210> SEQ ID NO 3
<211> LENGTH: 129
<212> TYPE: PRT
<213> ORGANISM: Bacteriophage R17

<400> SEQUENCE: 3

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Met Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr
```

```
<210> SEQ ID NO 4
<211> LENGTH: 130
<212> TYPE: PRT
<213> ORGANISM: Bacteriophage fr

<400> SEQUENCE: 4

Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Asn Asn Arg Lys Tyr Thr Val Lys Val Glu
    50                  55                  60

Val Pro Lys Val Ala Thr Gln Val Gln Gly Gly Val Glu Leu Pro Val
65                  70                  75                  80

Ala Ala Trp Arg Ser Tyr Met Asn Met Glu Leu Thr Ile Pro Val Phe
                85                  90                  95

Ala Thr Asn Asp Asp Cys Ala Leu Ile Val Lys Ala Leu Gln Gly Thr
            100                 105                 110

Phe Lys Thr Gly Asn Pro Ile Ala Thr Ala Ile Ala Ala Asn Ser Gly
        115                 120                 125

Ile Tyr
    130

<210> SEQ ID NO 5
<211> LENGTH: 130
<212> TYPE: PRT
<213> ORGANISM: Bacteriophage GA

<400> SEQUENCE: 5

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
            20                  25                  30

Leu Ser Asn Asn Ser Arg Ser Gln Ala Tyr Arg Val Thr Ala Ser Tyr
        35                  40                  45

Arg Ala Ser Gly Ala Asp Lys Arg Lys Tyr Ala Ile Lys Leu Glu Val
    50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130

<210> SEQ ID NO 6
<211> LENGTH: 132
<212> TYPE: PRT
<213> ORGANISM: Bacteriophage SP

<400> SEQUENCE: 6

Met Ala Lys Leu Asn Gln Val Thr Leu Ser Lys Ile Gly Lys Asn Gly
1               5                   10                  15
```

```
Asp Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Phe Lys
50                  55                  60

Val Gln Ile Lys Leu Gln Asn Pro Thr Ala Cys Thr Arg Asp Ala Cys
65                  70                  75                  80

Asp Pro Ser Val Thr Arg Ser Ala Phe Ala Asp Val Thr Leu Ser Phe
                85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
    130

<210> SEQ ID NO 7
<211> LENGTH: 329
<212> TYPE: PRT
<213> ORGANISM: Bacteriophage SP

<400> SEQUENCE: 7

Ala Lys Leu Asn Gln Val Thr Leu Ser Lys Ile Gly Lys Asn Gly Asp
1               5                   10                  15

Gln Thr Leu Thr Leu Thr Pro Arg Gly Val Asn Pro Thr Asn Gly Val
            20                  25                  30

Ala Ser Leu Ser Glu Ala Gly Ala Val Pro Ala Leu Glu Lys Arg Val
        35                  40                  45

Thr Val Ser Val Ala Gln Pro Ser Arg Asn Arg Lys Asn Phe Lys Val
50                  55                  60

Gln Ile Lys Leu Gln Asn Pro Thr Ala Cys Thr Arg Asp Ala Cys Asp
65                  70                  75                  80

Pro Ser Val Thr Arg Ser Ala Phe Ala Asp Val Thr Leu Ser Phe Thr
                85                  90                  95

Ser Tyr Ser Thr Asp Glu Glu Arg Ala Leu Ile Arg Thr Glu Leu Ala
            100                 105                 110

Ala Leu Leu Ala Asp Pro Leu Ile Val Asp Ala Ile Asp Asn Leu Asn
        115                 120                 125

Pro Ala Tyr Trp Ala Ala Leu Leu Val Ala Ser Ser Gly Gly Gly Asp
    130                 135                 140

Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
                165                 170                 175

Ser Ile Tyr Glu Val Gly Lys Glu Gly Ser Pro Asp Ile Tyr Glu Arg
            180                 185                 190

Gly Asp Glu Val Ser Val Thr Phe Asp Tyr Ala Leu Glu Asp Phe Leu
        195                 200                 205

Gly Asn Thr Asn Trp Arg Asn Trp Asp Gln Arg Leu Ser Tyr Asp
210                 215                 220

Ile Ala Asn Arg Arg Arg Cys Arg Gly Asn Gly Tyr Ile Asp Leu Asp
225                 230                 235                 240

Ala Thr Ala Met Gln Ser Asp Asp Phe Val Leu Ser Gly Arg Tyr Gly
                245                 250                 255
```

```
Val Arg Lys Val Lys Phe Pro Gly Ala Phe Gly Ser Ile Lys Tyr Leu
            260                 265                 270

Leu Asn Ile Gln Gly Asp Ala Trp Leu Asp Leu Ser Glu Val Thr Ala
            275                 280                 285

Tyr Arg Ser Tyr Gly Met Val Ile Gly Phe Trp Thr Asp Ser Lys Ser
            290                 295                 300

Pro Gln Leu Pro Thr Asp Phe Thr Gln Phe Asn Ser Ala Asn Cys Pro
305                 310                 315                 320

Val Gln Thr Val Ile Ile Pro Ser
                325

<210> SEQ ID NO 8
<211> LENGTH: 130
<212> TYPE: PRT
<213> ORGANISM: Bacteriophage MS2

<400> SEQUENCE: 8

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
            35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
            115                 120                 125

Ile Tyr
    130

<210> SEQ ID NO 9
<211> LENGTH: 133
<212> TYPE: PRT
<213> ORGANISM: Bacteriophage M11

<400> SEQUENCE: 9

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
            20                  25                  30

Val Ala Ala Leu Ser Glu Ala Gly Ala Val Pro Ala Leu Glu Lys Arg
            35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
            100                 105                 110

Leu Gln Ala Leu Leu Ala Asp Pro Met Leu Val Asn Ala Ile Asp Asn
```

```
Leu Asn Pro Ala Tyr
        130

<210> SEQ ID NO 10
<211> LENGTH: 133
<212> TYPE: PRT
<213> ORGANISM: Bacteriophage MX1

<400> SEQUENCE: 10

Met Ala Lys Leu Gln Ala Ile Thr Leu Ser Gly Ile Gly Lys Asn Gly
1               5                   10                  15

Asp Val Thr Leu Asn Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ala Asp Val Thr Phe Ser
                85                  90                  95

Phe Thr Gln Tyr Ser Thr Asp Glu Glu Arg Ala Leu Val Arg Thr Glu
            100                 105                 110

Leu Lys Ala Leu Leu Ala Asp Pro Met Leu Ile Asp Ala Ile Asp Asn
        115                 120                 125

Leu Asn Pro Ala Tyr
        130

<210> SEQ ID NO 11
<211> LENGTH: 330
<212> TYPE: PRT
<213> ORGANISM: Bacteriophage NL95

<400> SEQUENCE: 11

Met Ala Lys Leu Asn Lys Val Thr Leu Thr Gly Ile Gly Lys Ala Gly
1               5                   10                  15

Asn Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Tyr Lys
    50                  55                  60

Val Gln Ile Lys Leu Gln Asn Pro Thr Ala Cys Thr Lys Asp Ala Cys
65                  70                  75                  80

Asp Pro Ser Val Thr Arg Ser Gly Ser Arg Asp Val Thr Leu Ser Phe
                85                  90                  95

Thr Ser Tyr Ser Thr Glu Arg Glu Arg Ala Leu Ile Arg Thr Glu Leu
            100                 105                 110

Ala Ala Leu Leu Lys Asp Asp Leu Ile Val Asp Ala Ile Asp Asn Leu
        115                 120                 125

Asn Pro Ala Tyr Trp Ala Ala Leu Leu Ala Ala Ser Pro Gly Gly Gly
    130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
                165                 170                 175
```

```
Glu Leu Ile Thr Glu Ala Lys Asp Gly Ala Cys Ala Leu Tyr Ala Cys
            180                 185                 190

Gly Ser Glu Ala Leu Val Glu Phe Glu Tyr Ala Leu Glu Asp Phe Leu
        195                 200                 205

Gly Asn Glu Phe Trp Arg Asn Trp Asp Gly Arg Leu Ser Lys Tyr Asp
    210                 215                 220

Ile Glu Thr His Arg Arg Cys Arg Gly Asn Gly Tyr Val Asp Leu Asp
225                 230                 235                 240

Ala Ser Val Met Gln Ser Asp Glu Tyr Val Leu Ser Gly Ala Tyr Asp
                245                 250                 255

Val Val Lys Met Gln Pro Pro Gly Thr Phe Asp Ser Pro Arg Tyr Tyr
                260                 265                 270

Leu His Leu Met Asp Gly Ile Tyr Val Asp Leu Ala Glu Val Thr Ala
                275                 280                 285

Tyr Arg Ser Tyr Gly Met Val Ile Gly Phe Trp Thr Asp Ser Lys Ser
        290                 295                 300

Pro Gln Leu Pro Thr Asp Phe Thr Arg Phe Asn Arg His Asn Cys Pro
305                 310                 315                 320

Val Gln Thr Val Ile Val Ile Pro Ser Leu
                325                 330

<210> SEQ ID NO 12
<211> LENGTH: 129
<212> TYPE: PRT
<213> ORGANISM: Bacteriophage f2

<400> SEQUENCE: 12

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Leu Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

<210> SEQ ID NO 13
<211> LENGTH: 128
<212> TYPE: PRT
<213> ORGANISM: Bacteriophage PP7

<400> SEQUENCE: 13

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
```

-continued

```
                    35                  40                  45
Gly Ala Lys Thr Ala Tyr Arg Val Asn Leu Lys Leu Asp Gln Ala Asp
                50                  55                  60
Val Val Asp Cys Ser Thr Ser Val Cys Gly Glu Leu Pro Lys Val Arg
 65                  70                  75                  80
Tyr Thr Gln Val Trp Ser His Asp Val Thr Ile Val Ala Asn Ser Thr
                    85                  90                  95
Glu Ala Ser Arg Lys Ser Leu Tyr Asp Leu Thr Lys Ser Leu Val Ala
                100                 105                 110
Thr Ser Gln Val Glu Asp Leu Val Val Asn Leu Val Pro Leu Gly Arg
                115                 120                 125

<210> SEQ ID NO 14
<211> LENGTH: 131
<212> TYPE: PRT
<213> ORGANISM: bacteriophage AP205

<400> SEQUENCE: 14

Met Ala Asn Lys Pro Met Gln Pro Ile Thr Ser Thr Ala Asn Lys Ile
  1               5                  10                  15
Val Trp Ser Asp Pro Thr Arg Leu Ser Thr Thr Phe Ser Ala Ser Leu
                 20                  25                  30
Leu Arg Gln Arg Val Lys Val Gly Ile Ala Glu Leu Asn Asn Val Ser
                 35                  40                  45
Gly Gln Tyr Val Ser Val Tyr Lys Arg Pro Ala Pro Lys Pro Glu Gly
                 50                  55                  60
Cys Ala Asp Ala Cys Val Ile Met Pro Asn Glu Asn Gln Ser Ile Arg
 65                  70                  75                  80
Thr Val Ile Ser Gly Ser Ala Glu Asn Leu Ala Thr Leu Lys Ala Glu
                 85                  90                  95
Trp Glu Thr His Lys Arg Asn Val Asp Thr Leu Phe Ala Ser Gly Asn
                100                 105                 110
Ala Gly Leu Gly Phe Leu Asp Pro Thr Ala Ala Ile Val Ser Ser Asp
                115                 120                 125
Thr Thr Ala
          130

<210> SEQ ID NO 15
<211> LENGTH: 132
<212> TYPE: PRT
<213> ORGANISM: Artificial Sequence
<220> FEATURE:
<223> OTHER INFORMATION: Bacteriophage Qbeta 240 mutant

<400> SEQUENCE: 15

Ala Lys Leu Glu Thr Val Thr Leu Gly Asn Ile Gly Arg Asp Gly Lys
  1               5                  10                  15
Gln Thr Leu Val Leu Asn Pro Arg Gly Val Asn Pro Thr Asn Gly Val
                 20                  25                  30
Ala Ser Leu Ser Gln Ala Gly Ala Val Pro Ala Leu Glu Lys Arg Val
                 35                  40                  45
Thr Val Ser Val Ser Gln Pro Ser Arg Asn Arg Lys Asn Tyr Lys Val
                 50                  55                  60
Gln Val Lys Ile Gln Asn Pro Thr Ala Cys Thr Ala Asn Gly Ser Cys
 65                  70                  75                  80
Asp Pro Ser Val Thr Arg Gln Lys Tyr Ala Asp Val Thr Phe Ser Phe
                 85                  90                  95
```

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 16
<211> LENGTH: 132
<212> TYPE: PRT
<213> ORGANISM: Artificial Sequence
<220> FEATURE:
<223> OTHER INFORMATION: Bacteriophage Q-beta 243 mutant

<400> SEQUENCE: 16

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 17
<211> LENGTH: 132
<212> TYPE: PRT
<213> ORGANISM: Artificial Sequence
<220> FEATURE:
<223> OTHER INFORMATION: Bacteriophage Q-beta 250 mutant

<400> SEQUENCE: 17

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 18
<211> LENGTH: 132
<212> TYPE: PRT
<213> ORGANISM: Artificial Sequence
<220> FEATURE:
<223> OTHER INFORMATION: Bacteriophage Q-beta 251 mutant

<400> SEQUENCE: 18

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 19
<211> LENGTH: 132
<212> TYPE: PRT
<213> ORGANISM: Artificial Sequence
<220> FEATURE:
<223> OTHER INFORMATION: Bacteriophage Q-beta 259 mutant

<400> SEQUENCE: 19

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 20
<211> LENGTH: 185

```
<212> TYPE: PRT
<213> ORGANISM: Hepatitis B virus

<400> SEQUENCE: 20

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Asn Ala Pro Ile Leu Ser Thr Leu Pro
130                 135                 140

Glu Thr Thr Val Val Arg Arg Asp Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys
            180                 185

<210> SEQ ID NO 21
<211> LENGTH: 188
<212> TYPE: PRT
<213> ORGANISM: Hepatitis B virus

<400> SEQUENCE: 21

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Gly Gly
65                  70                  75                  80

Lys Gly Gly Ser Arg Asp Leu Val Val Ser Tyr Val Asn Thr Asn Val
                85                  90                  95

Gly Leu Lys Phe Arg Gln Leu Leu Trp Phe His Ile Ser Cys Leu Thr
            100                 105                 110

Phe Gly Arg Glu Thr Val Leu Glu Tyr Leu Val Ser Phe Gly Val Trp
        115                 120                 125

Ile Arg Thr Pro Pro Ala Tyr Arg Pro Asn Ala Pro Ile Leu Ser
130                 135                 140

Thr Leu Pro Glu Thr Thr Val Val Arg Arg Asp Arg Gly Arg Ser
145                 150                 155                 160

Pro Arg Arg Arg Thr Pro Ser Pro Arg Arg Arg Arg Ser Gln Ser Pro
```

Arg Arg Arg Arg Ser Gln Ser Arg Glu Ser Gln Cys
                180                 185

<210> SEQ ID NO 22
<211> LENGTH: 42
<212> TYPE: PRT
<213> ORGANISM: homo sapiens

<400> SEQUENCE: 22

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 23
<211> LENGTH: 42
<212> TYPE: PRT
<213> ORGANISM: Mus musculus

<400> SEQUENCE: 23

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg Gly Lys
            20                  25                  30

Lys Ser Asp Trp Lys His Asn Ile Thr Gln
        35                  40

<210> SEQ ID NO 24
<211> LENGTH: 42
<212> TYPE: PRT
<213> ORGANISM: Rattus

<400> SEQUENCE: 24

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Asn Asp Trp Lys His Asn Leu Thr Gln
        35                  40

<210> SEQ ID NO 25
<211> LENGTH: 42
<212> TYPE: PRT
<213> ORGANISM: Bos taurus

<400> SEQUENCE: 25

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Ile His Asn Ile Thr Gln
        35                  40

<210> SEQ ID NO 26
<211> LENGTH: 42
<212> TYPE: PRT
<213> ORGANISM: Sus scrofa

<400> SEQUENCE: 26

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
                20                  25                  30

Lys Ser Asp Trp Lys His Asn Ile Thr Gln
            35                  40

<210> SEQ ID NO 27
<211> LENGTH: 15
<212> TYPE: PRT
<213> ORGANISM: artificial sequence
<220> FEATURE:
<223> OTHER INFORMATION: GIP 1-15 (1)

<400> SEQUENCE: 27

Tyr Ala Glu Gly Thr Phe Ile Ser Asp Tyr Ser Ile Ala Met Asp
1               5                   10                  15

<210> SEQ ID NO 28
<211> LENGTH: 12
<212> TYPE: PRT
<213> ORGANISM: artificial sequence
<220> FEATURE:
<223> OTHER INFORMATION: GIP 31-42 (1)

<400> SEQUENCE: 28

Gly Lys Lys Asn Asp Trp Lys His Asn Ile Thr Gln
1               5                   10

<210> SEQ ID NO 29
<211> LENGTH: 10
<212> TYPE: PRT
<213> ORGANISM: artificial sequence
<220> FEATURE:
<223> OTHER INFORMATION: GIP 1-10

<400> SEQUENCE: 29

Tyr Ala Glu Gly Thr Phe Ile Ser Asp Tyr
1               5                   10

<210> SEQ ID NO 30
<211> LENGTH: 44
<212> TYPE: PRT
<213> ORGANISM: artificial sequence
<220> FEATURE:
<223> OTHER INFORMATION: mouse GIP GC

<400> SEQUENCE: 30

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg Gly Lys
                20                  25                  30

Lys Ser Asp Trp Lys His Asn Ile Thr Gln Gly Cys
            35                  40

<210> SEQ ID NO 31
<211> LENGTH: 15
<212> TYPE: PRT
<213> ORGANISM: artificial sequence
<220> FEATURE:
<223> OTHER INFORMATION: GIP 16-30 (1)

<400> SEQUENCE: 31

Lys Ile His Gln Gln Asp Phe Val Asn Trp Leu Leu Ala Gln Lys
1               5                   10                  15
```

```
<210> SEQ ID NO 32
<211> LENGTH: 10
<212> TYPE: PRT
<213> ORGANISM: artificial sequene
<220> FEATURE:
<223> OTHER INFORMATION: GIP 4-13

<400> SEQUENCE: 32

Gly Thr Phe Ile Ser Asp Tyr Ser Ile Ala
1               5                   10

<210> SEQ ID NO 33
<211> LENGTH: 28
<212> TYPE: PRT
<213> ORGANISM: homo sapiens

<400> SEQUENCE: 33

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 34
<211> LENGTH: 28
<212> TYPE: PRT
<213> ORGANISM: Mus musculus

<400> SEQUENCE: 34

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 35
<211> LENGTH: 28
<212> TYPE: PRT
<213> ORGANISM: Canis familiaris

<400> SEQUENCE: 35

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 36
<211> LENGTH: 8
<212> TYPE: PRT
<213> ORGANISM: artificial sequence
<220> FEATURE:
<223> OTHER INFORMATION: ghrel24-31

<400> SEQUENCE: 36

Gly Ser Ser Phe Leu Ser Pro Glu
1               5

<210> SEQ ID NO 37
<211> LENGTH: 7
<212> TYPE: PRT
<213> ORGANISM: artificial sequence
<220> FEATURE:
<223> OTHER INFORMATION: ghrel24-30

<400> SEQUENCE: 37

Gly Ser Ser Phe Leu Ser Pro
1               5
```

1          5

<210> SEQ ID NO 38
<211> LENGTH: 6
<212> TYPE: PRT
<213> ORGANISM: artificial sequence
<220> FEATURE:
<223> OTHER INFORMATION: ghrel24-29

<400> SEQUENCE: 38

Gly Ser Ser Phe Leu Ser
1               5

<210> SEQ ID NO 39
<211> LENGTH: 10
<212> TYPE: PRT
<213> ORGANISM: artificial sequence
<220> FEATURE:
<223> OTHER INFORMATION: Ghrel24-31 GC

<400> SEQUENCE: 39

Gly Ser Ser Phe Leu Ser Pro Glu Gly Cys
1               5                   10

<210> SEQ ID NO 40
<211> LENGTH: 28
<212> TYPE: PRT
<213> ORGANISM: Felis catus

<400> SEQUENCE: 40

Gly Ser Ser Phe Leu Ser Pro Glu His Gln Lys Val Gln Gln Arg Lys
1               5                   10                  15

Glu Ser Lys Lys Pro Pro Ala Lys Leu Gln Pro Arg
            20                  25

<210> SEQ ID NO 41
<211> LENGTH: 27
<212> TYPE: PRT
<213> ORGANISM: Bos taurus

<400> SEQUENCE: 41

Gly Ser Ser Phe Leu Ser Pro Glu His Gln Lys Leu Gln Arg Lys Glu
1               5                   10                  15

Ala Lys Lys Pro Ser Gly Arg Leu Lys Pro Arg
            20                  25

<210> SEQ ID NO 42
<211> LENGTH: 28
<212> TYPE: PRT
<213> ORGANISM: Sus scrofa

<400> SEQUENCE: 42

Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 43
<211> LENGTH: 15
<212> TYPE: PRT
<213> ORGANISM: artificial sequence
<220> FEATURE:
<223> OTHER INFORMATION: GIP 16-30 (2)

<400> SEQUENCE: 43

-continued

Lys Ile Arg Gln Gln Asp Phe Val Asn Trp Leu Leu Ala Gln Arg
1               5                   10                  15

<210> SEQ ID NO 44
<211> LENGTH: 12
<212> TYPE: PRT
<213> ORGANISM: artificial sequence
<220> FEATURE:
<223> OTHER INFORMATION: GIP 31-42 (2)

<400> SEQUENCE: 44

Gly Lys Lys Ser Asp Trp Lys His Asn Ile Thr Gln
1               5                   10

<210> SEQ ID NO 45
<211> LENGTH: 8
<212> TYPE: PRT
<213> ORGANISM: artificial sequence
<220> FEATURE:
<223> OTHER INFORMATION: GIP 4-11

<400> SEQUENCE: 45

Gly Thr Phe Ile Ser Asp Tyr Ser
1               5

<210> SEQ ID NO 46
<211> LENGTH: 13
<212> TYPE: PRT
<213> ORGANISM: Canis familiaris

<400> SEQUENCE: 46

Gly Ser Ser Phe Leu Ser Pro Glu His Gln Lys Leu Gln
1               5                   10

<210> SEQ ID NO 47
<211> LENGTH: 13
<212> TYPE: PRT
<213> ORGANISM: Felis catus

<400> SEQUENCE: 47

Gly Ser Ser Phe Leu Ser Pro Glu His Gln Lys Val Gln
1               5                   10

<210> SEQ ID NO 48
<211> LENGTH: 10
<212> TYPE: PRT
<213> ORGANISM: artificial sequence
<220> FEATURE:
<223> OTHER INFORMATION: gamma linker 1

<400> SEQUENCE: 48

Cys Gly Asp Lys Thr His Thr Ser Pro Pro
1               5                   10

<210> SEQ ID NO 49
<211> LENGTH: 6
<212> TYPE: PRT
<213> ORGANISM: artificial sequence
<220> FEATURE:
<223> OTHER INFORMATION: N terminial glycine linker

<400> SEQUENCE: 49

Gly Cys Gly Gly Gly Gly
1               5

<210> SEQ ID NO 50
<211> LENGTH: 6

```
<212> TYPE: PRT
<213> ORGANISM: artificial sequence
<220> FEATURE:
<223> OTHER INFORMATION: N-terminal glycine serine linker

<400> SEQUENCE: 50

Cys Gly Gly Gly Gly Ser
1               5

<210> SEQ ID NO 51
<211> LENGTH: 9
<212> TYPE: PRT
<213> ORGANISM: artificial sequence
<220> FEATURE:
<223> OTHER INFORMATION: GCGSGGGGS linker

<400> SEQUENCE: 51

Gly Cys Gly Ser Gly Gly Gly Gly Ser
1               5

<210> SEQ ID NO 52
<211> LENGTH: 10
<212> TYPE: PRT
<213> ORGANISM: artificial sequence
<220> FEATURE:
<223> OTHER INFORMATION: C-terminal gamma 1 linker

<400> SEQUENCE: 52

Asp Lys Thr His Thr Ser Pro Pro Cys Gly
1               5                   10

<210> SEQ ID NO 53
<211> LENGTH: 18
<212> TYPE: PRT
<213> ORGANISM: artificial sequence
<220> FEATURE:
<223> OTHER INFORMATION: C terminal gamma linker 3

<400> SEQUENCE: 53

Pro Lys Pro Ser Thr Pro Pro Gly Ser Ser Gly Gly Ala Pro Gly Gly
1               5                   10                  15

Cys Gly

<210> SEQ ID NO 54
<211> LENGTH: 6
<212> TYPE: PRT
<213> ORGANISM: artificial sequence
<220> FEATURE:
<223> OTHER INFORMATION: C terminal glycine linker

<400> SEQUENCE: 54

Gly Gly Gly Gly Cys Gly
1               5

<210> SEQ ID NO 55
<211> LENGTH: 6
<212> TYPE: PRT
<213> ORGANISM: artificial sequence
<220> FEATURE:
<223> OTHER INFORMATION: C terminal glycine serine linker

<400> SEQUENCE: 55

Ser Gly Gly Gly Gly Cys
1               5

<210> SEQ ID NO 56
<211> LENGTH: 10
```

```
<212> TYPE: PRT
<213> ORGANISM: artificial sequence
<220> FEATURE:
<223> OTHER INFORMATION: GSGGGGSGCG linker

<400> SEQUENCE: 56

Gly Ser Gly Gly Gly Gly Ser Gly Cys Gly
1               5                   10

<210> SEQ ID NO 57
<211> LENGTH: 6
<212> TYPE: PRT
<213> ORGANISM: artificial sequence
<220> FEATURE:
<223> OTHER INFORMATION: glycine lysine linker

<400> SEQUENCE: 57

Gly Gly Lys Lys Gly Cys
1               5

<210> SEQ ID NO 58
<211> LENGTH: 6
<212> TYPE: PRT
<213> ORGANISM: artificial sequence
<220> FEATURE:
<223> OTHER INFORMATION: glycine lysine linker 2

<400> SEQUENCE: 58

Cys Gly Lys Lys Gly Gly
1               5

<210> SEQ ID NO 59
<211> LENGTH: 17
<212> TYPE: PRT
<213> ORGANISM: artificial sequence
<220> FEATURE:
<223> OTHER INFORMATION: CGGPKPSTPPGSSGGAP

<400> SEQUENCE: 59

Cys Gly Gly Pro Lys Pro Ser Thr Pro Pro Gly Ser Ser Gly Gly Ala
1               5                   10                  15
Pro

<210> SEQ ID NO 60
<211> LENGTH: 17
<212> TYPE: PRT
<213> ORGANISM: artificial sequence
<220> FEATURE:
<223> OTHER INFORMATION: GIP 1-15GC

<400> SEQUENCE: 60

Tyr Ala Glu Gly Thr Phe Ile Ser Asp Tyr Ser Ile Ala Met Asp Gly
1               5                   10                  15
Cys

<210> SEQ ID NO 61
<211> LENGTH: 12
<212> TYPE: PRT
<213> ORGANISM: artificial sequence
<220> FEATURE:
<223> OTHER INFORMATION: GIP 1-10 GC

<400> SEQUENCE: 61

Tyr Ala Glu Gly Thr Phe Ile Ser Asp Tyr Gly Cys
1               5                   10
```

```
<210> SEQ ID NO 62
<211> LENGTH: 12
<212> TYPE: PRT
<213> ORGANISM: artificial sequence
<220> FEATURE:
<223> OTHER INFORMATION: GIP 4-13GC

<400> SEQUENCE: 62

Gly Thr Phe Ile Ser Asp Tyr Ser Ile Ala Gly Cys
1               5                   10

<210> SEQ ID NO 63
<211> LENGTH: 42
<212> TYPE: PRT
<213> ORGANISM: Felis catus

<400> SEQUENCE: 63

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Lys His Asn Ile Thr Gln
        35                  40

<210> SEQ ID NO 64
<211> LENGTH: 4
<212> TYPE: PRT
<213> ORGANISM: artificial sequence
<220> FEATURE:
<223> OTHER INFORMATION: GIP 7-10

<400> SEQUENCE: 64

Ile Ser Asp Tyr
1

<210> SEQ ID NO 65
<211> LENGTH: 9
<212> TYPE: PRT
<213> ORGANISM: artificial sequence
<220> FEATURE:
<223> OTHER INFORMATION: GIP 7-15

<400> SEQUENCE: 65

Ile Ser Asp Tyr Ser Ile Ala Met Asp
1               5

<210> SEQ ID NO 66
<211> LENGTH: 12
<212> TYPE: PRT
<213> ORGANISM: artificial sequence
<220> FEATURE:
<223> OTHER INFORMATION: GIP 7-15

<400> SEQUENCE: 66

Gly Thr Phe Ile Ser Asp Tyr Ser Ile Ala Met Asp
1               5                   10

<210> SEQ ID NO 67
<211> LENGTH: 7
<212> TYPE: PRT
<213> ORGANISM: artificial sequence
<220> FEATURE:
<223> OTHER INFORMATION: GIP 4-10

<400> SEQUENCE: 67

Gly Thr Phe Ile Ser Asp Tyr
1               5
```

<210> SEQ ID NO 68
<211> LENGTH: 15
<212> TYPE: PRT
<213> ORGANISM: artificial sequence
<220> FEATURE:
<223> OTHER INFORMATION: GIP human 28-42

<400> SEQUENCE: 68

Ala Gln Lys Gly Lys Lys Asn Asp Trp Lys His Asn Ile Thr Gln
1               5                   10                  15

<210> SEQ ID NO 69
<211> LENGTH: 16
<212> TYPE: PRT
<213> ORGANISM: artificial sequence
<220> FEATURE:
<223> OTHER INFORMATION: GIP 1-14DD

<400> SEQUENCE: 69

Tyr Ala Glu Gly Thr Phe Ile Ser Asp Tyr Ser Ile Ala Met Asp Asp
1               5                   10                  15

<210> SEQ ID NO 70
<211> LENGTH: 16
<212> TYPE: PRT
<213> ORGANISM: artificial sequence
<220> FEATURE:
<223> OTHER INFORMATION: GIP 1-14KK

<400> SEQUENCE: 70

Tyr Ala Glu Gly Thr Phe Ile Ser Asp Tyr Ser Ile Ala Met Lys Lys
1               5                   10                  15

<210> SEQ ID NO 71
<211> LENGTH: 17
<212> TYPE: PRT
<213> ORGANISM: artificial sequence
<220> FEATURE:
<223> OTHER INFORMATION: GIP 1-15 DD

<400> SEQUENCE: 71

Tyr Ala Glu Gly Thr Phe Ile Ser Asp Tyr Ser Ile Ala Met Asp Asp
1               5                   10                  15

Asp

<210> SEQ ID NO 72
<211> LENGTH: 17
<212> TYPE: PRT
<213> ORGANISM: artificial sequence
<220> FEATURE:
<223> OTHER INFORMATION: GIP 1-15KK

<400> SEQUENCE: 72

Tyr Ala Glu Gly Thr Phe Ile Ser Asp Tyr Ser Ile Ala Met Asp Lys
1               5                   10                  15

Lys

<210> SEQ ID NO 73
<211> LENGTH: 30
<212> TYPE: DNA
<213> ORGANISM: artificial sequence
<220> FEATURE:
<223> OTHER INFORMATION: oligo p1.45

<400> SEQUENCE: 73

```
aatctagaat tttctgcgca cccatcccgg                                          30

<210> SEQ ID NO 74
<211> LENGTH: 39
<212> TYPE: DNA
<213> ORGANISM: artificial sequence
<220> FEATURE:
<223> OTHER INFORMATION: oligo p4.175

<400> SEQUENCE: 74
aatgaacgtg ccctctgcgt atccggaacc gcctcctgc                                39

<210> SEQ ID NO 75
<211> LENGTH: 42
<212> TYPE: DNA
<213> ORGANISM: artificial sequence
<220> FEATURE:
<223> OTHER INFORMATION: oligo p4.176

<400> SEQUENCE: 75
catcgcgatc gagtaatcgg aaatgaacgt gccctctgcg ta                            42

<210> SEQ ID NO 76
<211> LENGTH: 31
<212> TYPE: DNA
<213> ORGANISM: artificial sequence
<220> FEATURE:
<223> OTHER INFORMATION: oligo p4.177

<400> SEQUENCE: 76
acatgcatta atccatcgcg atcgagtaat c                                        31
```